US012648850B2

(12) United States Patent
Galler et al.

(10) Patent No.: US 12,648,850 B2
(45) Date of Patent: Jun. 9, 2026

(54) SYSTEMS AND METHODS FOR TARGET/ARTICLE BRIDGING ENGAGEMENT AND ANCHORING

(71) Applicant: VALCARE MEDICAL, INC., Wilmington, DE (US)

(72) Inventors: Aviad Galler, Tel Aviv (IL); Nadav Yellin, Even Yehuda (IL); Yoav Rozen, Binyamina (IL); Shuki Porath, Haifa (IL)

(73) Assignee: Valcare Medical, Inc., Wilmington, DE (US)

( * ) Notice: Subject to any disclaimer, the term of this patent is extended or adjusted under 35 U.S.C. 154(b) by 883 days.

(21) Appl. No.: 17/817,791

(22) Filed: Aug. 5, 2022

(65) Prior Publication Data

US 2023/0045532 A1 Feb. 9, 2023

Related U.S. Application Data

(60) Provisional application No. 63/260,085, filed on Aug. 9, 2021.

(51) Int. Cl.
*A61F 2/24* (2006.01)

(52) U.S. Cl.
CPC .......... *A61F 2/2466* (2013.01); *A61F 2/2445* (2013.01); *A61F 2220/0016* (2013.01)

(58) Field of Classification Search
CPC ...................... A61F 2/2409; A61F 2/24; A61F 2/2442–2/2466; A61B 2017/0412;
(Continued)

(56) References Cited

U.S. PATENT DOCUMENTS 4,164,046 A 8/1979 Cooley
4,602,911 A 7/1986 Ahmadi et al.
(Continued)

FOREIGN PATENT DOCUMENTS

CN 2114422 U 9/1992
CN 2633218 Y 8/2004
(Continued)

OTHER PUBLICATIONS

PCT/IL2022/050868, International Search Report and Written Opinion, Nov. 17, 2022, 19 pages.
(Continued)

*Primary Examiner* — Alvin J Stewart
(74) *Attorney, Agent, or Firm* — Greenberg Traurig, LLP; Christopher C. Bolten; Robert D. Ward

(57) ABSTRACT

A system for bridging a gap between an article or a portion thereof and a target, and anchoring the article or its portion to the target, the system comprising a) an elongated delivery catheter having a distal end; b) and a bridging and anchoring construction, operable to selectably translate in a distal and a proximal direction relative to the distal end of the elongated delivery catheter, the bridging and anchoring construction slidably coupled to the elongated delivery catheter, wherein the bridging and anchoring construction is operable to 1) engage the target following the distal translation spanning the gap between the article or its portion and the target; 2) eliminating the gap following the proximal translation; and 3) anchoring the article or its portion to the target.

39 Claims, 10 Drawing Sheets

(58) Field of Classification Search
CPC .. A61B 2017/0427; A61B 2017/00243; A61B
2017/00579
See application file for complete search history.

(56) References Cited

U.S. PATENT DOCUMENTS

| | | | |
|---|---|---|---|
| 4,874,378 | A | 10/1989 | Hillstead |
| 4,953,540 | A | 9/1990 | Ray et al. |
| 5,080,662 | A | 1/1992 | Paul |
| 5,236,440 | A | 8/1993 | Hlavacek |
| 5,306,296 | A | 4/1994 | Wright et al. |
| D376,206 | S | 12/1996 | Reif |
| 5,609,565 | A | 3/1997 | Nakamura |
| 5,695,518 | A | 12/1997 | Laerum |
| 5,716,370 | A | 2/1998 | Williamson, IV et al. |
| 5,855,614 | A | 1/1999 | Stevens et al. |
| D410,543 | S | 6/1999 | Reif |
| 6,113,611 | A | 9/2000 | Allen et al. |
| 6,231,602 | B1 | 5/2001 | Carpentier et al. |
| 6,447,524 | B1* | 9/2002 | Knodel .............. A61B 17/0682 606/232 |
| D471,981 | S | 3/2003 | Reif |
| 6,619,291 | B2 | 9/2003 | Hlavka et al. |
| 6,629,534 | B1 | 10/2003 | St. Goar et al. |
| 6,669,687 | B1 | 12/2003 | Saadat |
| 6,689,048 | B2 | 2/2004 | Vanden Hoek et al. |
| 6,726,704 | B1* | 4/2004 | Loshakove ........ A61B 17/0057 606/213 |
| 6,776,784 | B2 | 8/2004 | Ginn |
| 6,790,229 | B1 | 9/2004 | Berreklouw |
| 6,797,002 | B2 | 9/2004 | Spence et al. |
| 6,805,711 | B2 | 10/2004 | Quijano et al. |
| 6,869,444 | B2 | 3/2005 | Gabbay |
| 6,893,459 | B1 | 5/2005 | Macoviak |
| 7,101,395 | B2 | 9/2006 | Tremulis et al. |
| 7,114,953 | B1 | 10/2006 | Wagner |
| 7,175,660 | B2 | 2/2007 | Cartledge et al. |
| 7,238,191 | B2 | 7/2007 | Bachmann |
| 7,285,087 | B2 | 10/2007 | Moaddeb et al. |
| 7,297,150 | B2 | 11/2007 | Cartledge et al. |
| 7,569,072 | B2 | 8/2009 | Berg et al. |
| 7,594,887 | B2 | 9/2009 | Moaddeb et al. |
| 7,635,329 | B2 | 12/2009 | Goldfarb et al. |
| 7,655,040 | B2 | 2/2010 | Douk et al. |
| 7,717,954 | B2 | 5/2010 | Solem et al. |
| 7,722,668 | B2 | 5/2010 | Moaddeb et al. |
| 7,758,637 | B2 | 7/2010 | Starksen et al. |
| 7,828,819 | B2 | 11/2010 | Webler et al. |
| 7,837,729 | B2 | 11/2010 | Gordon et al. |
| D642,683 | S | 8/2011 | Drake |
| 7,988,725 | B2* | 8/2011 | Gross ................... A61F 2/2445 623/2.37 |
| 8,163,014 | B2 | 4/2012 | Lane et al. |
| 8,182,529 | B2 | 5/2012 | Gordon et al. |
| 8,236,049 | B2 | 8/2012 | Rowe et al. |
| 8,287,591 | B2 | 10/2012 | Keidar et al. |
| 8,333,204 | B2 | 12/2012 | Saadat |
| 8,518,107 | B2 | 8/2013 | Tsukashima et al. |
| 8,579,968 | B1 | 11/2013 | Shannon et al. |
| 8,690,939 | B2 | 4/2014 | Miller et al. |
| 8,821,570 | B2 | 9/2014 | DuMontelle et al. |
| 9,180,008 | B2 | 11/2015 | Yellin et al. |
| 9,402,721 | B2 | 8/2016 | Buchbinder et al. |
| 9,433,503 | B2 | 9/2016 | Tsukashima et al. |
| 9,839,519 | B2 | 12/2017 | Shaolian et al. |
| 9,877,833 | B1 | 1/2018 | Bishop et al. |
| D858,771 | S | 9/2019 | Kugler et al. |
| 10,405,979 | B2 | 9/2019 | Schaffner et al. |
| 10,543,087 | B2 | 1/2020 | Yellin et al. |
| 10,779,945 | B2 | 9/2020 | Buchbinder et al. |
| 11,058,417 | B2 | 7/2021 | Foerster et al. |
| 11,191,536 | B2 | 12/2021 | Foerster et al. |
| 11,224,422 | B2 | 1/2022 | Foerster et al. |
| 11,298,230 | B2 | 4/2022 | Shaolian et al. |
| 11,382,749 | B2 | 7/2022 | Yellin et al. |

| | | | |
|---|---|---|---|
| D964,567 | S | 9/2022 | Ito |
| 11,510,835 | B2 | 11/2022 | Yellin et al. |
| 11,534,300 | B2 | 12/2022 | Yellin et al. |
| 11,571,301 | B2 | 2/2023 | Yellin et al. |
| 11,571,307 | B2 | 2/2023 | Yellin et al. |
| 11,576,779 | B2 | 2/2023 | Yellin et al. |
| 11,617,647 | B2 | 4/2023 | Yellin |
| 11,654,018 | B2 | 5/2023 | Shaolian et al. |
| 11,793,628 | B2 | 10/2023 | Dumontelle et al. |
| 11,806,009 | B2 | 11/2023 | Foerster et al. |
| 11,806,237 | B2 | 11/2023 | Rozen et al. |
| 11,813,164 | B2 | 11/2023 | Yellin et al. |
| 11,857,418 | B2* | 1/2024 | Yellin .............. A61B 17/12122 |
| 12,115,069 | B2 | 10/2024 | Shaolian et al. |
| 12,127,941 | B2 | 10/2024 | Yellin et al. |
| 12,279,955 | B2 | 4/2025 | Yellin et al. |
| 2001/0049557 | A1 | 12/2001 | Chinn et al. |
| 2002/0026214 | A1 | 2/2002 | Tanner et al. |
| 2002/0151961 | A1 | 10/2002 | Lashinski et al. |
| 2002/0151970 | A1 | 10/2002 | Garrison et al. |
| 2002/0188170 | A1 | 12/2002 | Santamore et al. |
| 2002/0198526 | A1 | 12/2002 | Shaolian et al. |
| 2003/0050649 | A1 | 3/2003 | Brock et al. |
| 2003/0050693 | A1 | 3/2003 | Quijano et al. |
| 2003/0078465 | A1 | 4/2003 | Pai et al. |
| 2003/0078671 | A1 | 4/2003 | Lesniak et al. |
| 2003/0191528 | A1 | 10/2003 | Quijano et al. |
| 2003/0198605 | A1 | 10/2003 | Montgomery |
| 2003/0199974 | A1 | 10/2003 | Lee et al. |
| 2004/0044364 | A1 | 3/2004 | DeVries et al. |
| 2004/0068276 | A1 | 4/2004 | Golden et al. |
| 2004/0073237 | A1 | 4/2004 | Leinsing |
| 2004/0122514 | A1 | 6/2004 | Fogarty et al. |
| 2004/0138744 | A1 | 7/2004 | Lashinski et al. |
| 2004/0148021 | A1 | 7/2004 | Cartledge et al. |
| 2004/0193191 | A1 | 9/2004 | Starksen et al. |
| 2004/0243230 | A1 | 12/2004 | Navia et al. |
| 2004/0249391 | A1 | 12/2004 | Cummins |
| 2004/0260393 | A1 | 12/2004 | Rahdert et al. |
| 2004/0260394 | A1 | 12/2004 | Douk et al. |
| 2005/0004668 | A1 | 1/2005 | Aklog et al. |
| 2005/0020696 | A1 | 1/2005 | Montgomery et al. |
| 2005/0033325 | A1 | 2/2005 | May et al. |
| 2005/0065550 | A1 | 3/2005 | Starksen et al. |
| 2005/0090846 | A1 | 4/2005 | Pedersen et al. |
| 2005/0096740 | A1 | 5/2005 | Langberg et al. |
| 2005/0113910 | A1 | 5/2005 | Paniagua et al. |
| 2005/0137692 | A1 | 6/2005 | Haug et al. |
| 2005/0137695 | A1 | 6/2005 | Salahieh et al. |
| 2005/0203549 | A1 | 9/2005 | Realyvasquez |
| 2005/0222678 | A1 | 10/2005 | Lashinski et al. |
| 2005/0240200 | A1 | 10/2005 | Bergheim |
| 2005/0250161 | A1 | 11/2005 | Suciu-Foca et al. |
| 2005/0267572 | A1 | 12/2005 | Schoon et al. |
| 2005/0283190 | A1 | 12/2005 | Huitema et al. |
| 2005/0288778 | A1 | 12/2005 | Shaoulian et al. |
| 2005/0288781 | A1 | 12/2005 | Moaddeb et al. |
| 2006/0009737 | A1 | 1/2006 | Whiting et al. |
| 2006/0020327 | A1 | 1/2006 | Lashinski et al. |
| 2006/0020334 | A1 | 1/2006 | Lashinski et al. |
| 2006/0052867 | A1 | 3/2006 | Revuelta et al. |
| 2006/0122633 | A1 | 6/2006 | To et al. |
| 2006/0129025 | A1 | 6/2006 | Levine et al. |
| 2006/0155165 | A1 | 7/2006 | Vanden Hoek et al. |
| 2006/0161169 | A1 | 7/2006 | Nieminen et al. |
| 2006/0184240 | A1 | 8/2006 | Jimenez et al. |
| 2006/0184242 | A1 | 8/2006 | Lichtenstein |
| 2006/0195134 | A1 | 8/2006 | Crittenden |
| 2006/0195183 | A1 | 8/2006 | Navia et al. |
| 2006/0241748 | A1 | 10/2006 | Lee et al. |
| 2006/0282161 | A1 | 12/2006 | Huynh et al. |
| 2007/0016287 | A1 | 1/2007 | Cartledge et al. |
| 2007/0027533 | A1 | 2/2007 | Douk |
| 2007/0038296 | A1 | 2/2007 | Navia |
| 2007/0051377 | A1 | 3/2007 | Douk et al. |
| 2007/0067027 | A1 | 3/2007 | Moaddeb et al. |
| 2007/0073098 | A1 | 3/2007 | Lenker et al. |
| 2007/0080188 | A1 | 4/2007 | Spence et al. |
| 2007/0093854 | A1 | 4/2007 | Kayan |

(56)  References Cited

U.S. PATENT DOCUMENTS

| | | | |
|---|---|---|---|
| 2007/0118215 A1 | 5/2007 | Moaddeb | |
| 2007/0128132 A1 | 6/2007 | Piergallini et al. | |
| 2007/0135913 A1 | 6/2007 | Moaddeb et al. | |
| 2007/0142907 A1 | 6/2007 | Moaddeb et al. | |
| 2007/0213812 A1 | 9/2007 | Webler et al. | |
| 2007/0233239 A1 | 10/2007 | Navia et al. | |
| 2007/0239272 A1 | 10/2007 | Navia et al. | |
| 2007/0244553 A1 | 10/2007 | Rafiee et al. | |
| 2007/0244554 A1 | 10/2007 | Rafiee et al. | |
| 2007/0244555 A1 | 10/2007 | Rafiee et al. | |
| 2007/0244556 A1 | 10/2007 | Rafiee et al. | |
| 2007/0250161 A1 | 10/2007 | Dolan | |
| 2007/0293942 A1 | 12/2007 | Mirzaee | |
| 2008/0039934 A1 | 2/2008 | Styrc | |
| 2008/0051807 A1 | 2/2008 | St. Goar et al. | |
| 2008/0065011 A1 | 3/2008 | Marchand et al. | |
| 2008/0177380 A1 | 7/2008 | Starksen et al. | |
| 2008/0177381 A1 | 7/2008 | Navia et al. | |
| 2008/0200980 A1 | 8/2008 | Robin et al. | |
| 2008/0208327 A1 | 8/2008 | Rowe | |
| 2008/0215145 A1 | 9/2008 | Moaddeb et al. | |
| 2008/0243220 A1 | 10/2008 | Barker | |
| 2008/0262513 A1 | 10/2008 | Stahler et al. | |
| 2008/0262609 A1 | 10/2008 | Gross et al. | |
| 2008/0288060 A1* | 11/2008 | Kaye | A61B 17/0401 |
| | | | 623/2.36 |
| 2008/0306586 A1 | 12/2008 | Cartledge et al. | |
| 2009/0076599 A1 | 3/2009 | Bergin | |
| 2009/0088838 A1 | 4/2009 | Shaolian et al. | |
| 2009/0118747 A1 | 5/2009 | Bettuchi et al. | |
| 2009/0125098 A1 | 5/2009 | Chuter | |
| 2009/0149872 A1 | 6/2009 | Gross et al. | |
| 2009/0216322 A1 | 8/2009 | Le et al. | |
| 2009/0222083 A1 | 9/2009 | Nguyen et al. | |
| 2009/0238778 A1 | 9/2009 | Mordas et al. | |
| 2009/0299470 A1 | 12/2009 | Rao et al. | |
| 2010/0010616 A1 | 1/2010 | Drews et al. | |
| 2010/0030014 A1 | 2/2010 | Ferrazzi | |
| 2010/0063586 A1 | 3/2010 | Hasenkam et al. | |
| 2010/0076549 A1 | 3/2010 | Keidar et al. | |
| 2010/0121433 A1 | 5/2010 | Bolling et al. | |
| 2010/0161047 A1* | 6/2010 | Cabiri | A61B 17/068 |
| | | | 623/2.37 |
| 2010/0185274 A1 | 7/2010 | Moaddeb et al. | |
| 2010/0191327 A1 | 7/2010 | Lane et al. | |
| 2010/0204713 A1 | 8/2010 | Ruiz Morales | |
| 2010/0211166 A1 | 8/2010 | Miller et al. | |
| 2010/0249920 A1 | 9/2010 | Bolling et al. | |
| 2010/0262232 A1 | 10/2010 | Annest | |
| 2010/0266989 A1 | 10/2010 | Piergallini et al. | |
| 2010/0280604 A1 | 11/2010 | Zipory et al. | |
| 2010/0280605 A1 | 11/2010 | Hammer et al. | |
| 2010/0286767 A1 | 11/2010 | Zipory et al. | |
| 2011/0004299 A1 | 1/2011 | Navia et al. | |
| 2011/0011917 A1* | 1/2011 | Loulmet | A61F 2/2457 |
| | | | 227/181.1 |
| 2011/0022168 A1 | 1/2011 | Cartledge | |
| 2011/0027753 A1 | 2/2011 | Maurat et al. | |
| 2011/0034953 A1 | 2/2011 | Milo | |
| 2011/0034999 A1 | 2/2011 | Carpentier et al. | |
| 2011/0060407 A1 | 3/2011 | Ketai et al. | |
| 2011/0066231 A1 | 3/2011 | Cartledge et al. | |
| 2011/0093062 A1 | 4/2011 | Cartledge et al. | |
| 2011/0106245 A1 | 5/2011 | Miller et al. | |
| 2011/0106247 A1 | 5/2011 | Miller et al. | |
| 2011/0137397 A1 | 6/2011 | Chau et al. | |
| 2011/0166649 A1 | 7/2011 | Gross et al. | |
| 2011/0190879 A1 | 8/2011 | Bobo et al. | |
| 2011/0208295 A1 | 8/2011 | Cartledge et al. | |
| 2011/0208298 A1 | 8/2011 | Tuval et al. | |
| 2011/0224785 A1 | 9/2011 | Hacohen | |
| 2011/0257728 A1 | 10/2011 | Kuehn | |
| 2011/0282361 A1 | 11/2011 | Miller et al. | |
| 2011/0301698 A1 | 12/2011 | Miller et al. | |
| 2011/0301699 A1 | 12/2011 | Saadat | |
| 2011/0319989 A1 | 12/2011 | Lane et al. | |
| 2012/0022557 A1 | 1/2012 | Cabiri et al. | |
| 2012/0022639 A1 | 1/2012 | Hacohen et al. | |
| 2012/0022644 A1 | 1/2012 | Reich et al. | |
| 2012/0053687 A1 | 3/2012 | Migliazza et al. | |
| 2012/0059458 A1 | 3/2012 | Buchbinder et al. | |
| 2012/0083806 A1 | 4/2012 | Goertzen | |
| 2012/0083880 A1 | 4/2012 | Rankin et al. | |
| 2012/0095455 A1 | 4/2012 | Rodmond et al. | |
| 2012/0123531 A1 | 5/2012 | Tsukashima et al. | |
| 2012/0136436 A1 | 5/2012 | Cabiri et al. | |
| 2012/0136463 A1 | 5/2012 | Muniz | |
| 2012/0165930 A1 | 6/2012 | Gifford, III et al. | |
| 2012/0245604 A1* | 9/2012 | Tegzes | A61B 17/0401 |
| | | | 606/151 |
| 2012/0310330 A1 | 12/2012 | Buchbinder et al. | |
| 2013/0066342 A1 | 3/2013 | Dell et al. | |
| 2013/0087598 A1 | 4/2013 | Surti | |
| 2013/0116780 A1 | 5/2013 | Miller et al. | |
| 2013/0166022 A1 | 6/2013 | Conklin | |
| 2013/0204361 A1 | 8/2013 | Adams et al. | |
| 2013/0226289 A1 | 8/2013 | Shaolian et al. | |
| 2013/0226290 A1 | 8/2013 | Yellin et al. | |
| 2013/0282114 A1 | 10/2013 | Schweich, Jr. et al. | |
| 2013/0289718 A1 | 10/2013 | Tsukashima et al. | |
| 2013/0289720 A1 | 10/2013 | Dobrilovic | |
| 2013/0304197 A1 | 11/2013 | Buchbinder et al. | |
| 2014/0005778 A1 | 1/2014 | Buchbinder et al. | |
| 2014/0025163 A1 | 1/2014 | Padala et al. | |
| 2014/0046433 A1 | 2/2014 | Kovalsky | |
| 2014/0058505 A1 | 2/2014 | Bielefeld | |
| 2014/0114407 A1 | 4/2014 | Rajamannan | |
| 2014/0188130 A1 | 7/2014 | Sanchez et al. | |
| 2014/0214157 A1 | 7/2014 | Börtlein et al. | |
| 2014/0277411 A1 | 9/2014 | Börtlein et al. | |
| 2014/0277420 A1 | 9/2014 | Migliazza et al. | |
| 2014/0364939 A1 | 12/2014 | Deshmukh et al. | |
| 2015/0073420 A1 | 3/2015 | Bookwalter et al. | |
| 2015/0112432 A1 | 4/2015 | Reich et al. | |
| 2015/0127093 A1 | 5/2015 | Hosmer et al. | |
| 2015/0173897 A1 | 6/2015 | Raanani et al. | |
| 2015/0173987 A1 | 6/2015 | Albinmousa et al. | |
| 2015/0351903 A1 | 12/2015 | Morriss et al. | |
| 2015/0366666 A1 | 12/2015 | Khairkhahan et al. | |
| 2016/0022419 A1 | 1/2016 | Yellin et al. | |
| 2016/0038286 A1 | 2/2016 | Yellin et al. | |
| 2016/0089235 A1 | 3/2016 | Yellin | |
| 2016/0100897 A1 | 4/2016 | Avalos et al. | |
| 2016/0106420 A1 | 4/2016 | Foerster et al. | |
| 2016/0120642 A1 | 5/2016 | Shaolian et al. | |
| 2016/0120645 A1* | 5/2016 | Alon | A61F 2/2442 |
| | | | 623/2.4 |
| 2016/0220371 A1 | 8/2016 | Keane | |
| 2016/0270911 A1 | 9/2016 | Ganesan et al. | |
| 2016/0331534 A1 | 11/2016 | Buchbinder et al. | |
| 2017/0042670 A1 | 2/2017 | Shaolian et al. | |
| 2017/0231763 A1 | 8/2017 | Yellin | |
| 2017/0258590 A1 | 9/2017 | Khairkhahan | |
| 2017/0296340 A1 | 10/2017 | Gross et al. | |
| 2017/0325948 A1 | 11/2017 | Wallace et al. | |
| 2018/0028387 A1 | 2/2018 | Yellin et al. | |
| 2018/0042723 A1 | 2/2018 | Yellin et al. | |
| 2018/0098849 A1 | 4/2018 | Yellin et al. | |
| 2018/0161160 A1 | 6/2018 | Shaolian et al. | |
| 2018/0161161 A1 | 6/2018 | Yellin et al. | |
| 2018/0228610 A1 | 8/2018 | Lashinski et al. | |
| 2018/0235758 A1 | 8/2018 | Biadillah et al. | |
| 2018/0325670 A1 | 11/2018 | De | |
| 2019/0053905 A1* | 2/2019 | Alon | A61F 2/2409 |
| 2019/0083091 A1* | 3/2019 | Foerster | A61B 17/068 |
| 2019/0083092 A1 | 3/2019 | Foerster et al. | |
| 2019/0083239 A1 | 3/2019 | Shaolian et al. | |
| 2019/0083240 A1 | 3/2019 | Shaolian et al. | |
| 2019/0091022 A1 | 3/2019 | Yellin et al. | |
| 2019/0133765 A1 | 5/2019 | Yellin et al. | |
| 2020/0069426 A1 | 3/2020 | Conklin et al. | |
| 2020/0138577 A1 | 5/2020 | Smolinsky | |
| 2020/0163763 A1 | 5/2020 | Zipory et al. | |
| 2020/0170799 A1 | 6/2020 | Yellin et al. | |

(56) References Cited

U.S. PATENT DOCUMENTS

| | | | |
|---|---|---|---|
| 2020/0237516 A1 | 7/2020 | Sampson et al. | |
| 2020/0330228 A1 | 10/2020 | Anderson et al. | |
| 2021/0015609 A1 | 1/2021 | Dumontelle et al. | |
| 2021/0085463 A1 | 3/2021 | Yellin et al. | |
| 2021/0161662 A1 | 6/2021 | Albes | |
| 2021/0346159 A1 | 11/2021 | Keränen | |
| 2021/0353417 A1 | 11/2021 | Yellin et al. | |
| 2022/0096237 A1* | 3/2022 | Hiorth | A61F 2/2457 |
| 2022/0226116 A1 | 7/2022 | Colli et al. | |
| 2022/0226771 A1 | 7/2022 | Lipscomb | |
| 2023/0040083 A1 | 2/2023 | Gifford, III et al. | |
| 2023/0285148 A1 | 9/2023 | Yellin et al. | |
| 2023/0372086 A1 | 11/2023 | Galler et al. | |
| 2024/0307182 A1 | 9/2024 | Colli et al. | |
| 2025/0114202 A1* | 4/2025 | Whitman | A61B 17/0467 |

FOREIGN PATENT DOCUMENTS

| | | | | |
|---|---|---|---|---|
| CN | 101411632 A | 4/2009 | | |
| CN | 101460113 A | 6/2009 | | |
| CN | 101553190 A | 10/2009 | | |
| CN | 102014797 A | 4/2011 | | |
| CN | 102088930 A | 6/2011 | | |
| CN | 202859386 U | 4/2013 | | |
| CN | 103179920 A | 6/2013 | | |
| CN | 103237523 A | 8/2013 | | |
| CN | 103735337 A | 4/2014 | | |
| CN | 203954080 U | 11/2014 | | |
| CN | 108618871 A | 10/2018 | | |
| CN | 113855324 A | 12/2021 | | |
| CN | 116269941 A * | 6/2023 | | A61B 17/0401 |
| DE | 102014102653 A1 | 9/2015 | | |
| EP | 1752115 A1 | 2/2007 | | |
| EP | 2471464 A1 | 7/2012 | | |
| EP | 2600799 A2 | 6/2013 | | |
| EP | 2928538 A1 | 10/2015 | | |
| EP | 2967700 A1 | 1/2016 | | |
| EP | 2600799 B1 | 5/2017 | | |
| EP | 3213715 A1 | 9/2017 | | |
| EP | 2928538 B1 | 11/2018 | | |
| FR | 2845889 A1 | 4/2004 | | |
| GB | 1496804 A | 1/1978 | | |
| GB | 2366319 A | 3/2002 | | |
| GB | 2601146 A * | 5/2022 | | A61B 17/0401 |
| KR | 20040095482 A | 11/2004 | | |
| RU | 125062 U1 | 2/2013 | | |
| WO | WO-8000673 A1 | 4/1980 | | |
| WO | WO-9009153 A1 | 8/1990 | | |
| WO | WO-9728745 A1 | 8/1997 | | |
| WO | WO-03017874 A1 | 3/2003 | | |
| WO | WO-03047467 A1 | 6/2003 | | |
| WO | WO-2005046488 A2 | 5/2005 | | |
| WO | WO-2007035882 A2 | 3/2007 | | |
| WO | WO-2008097999 A2 | 8/2008 | | |
| WO | WO-2009052427 A1 | 4/2009 | | |
| WO | WO-2009120764 A2 | 10/2009 | | |
| WO | WO-2010004546 A1 | 1/2010 | | |
| WO | WO-2010085659 A1 | 7/2010 | | |
| WO | WO-2011011443 A2 | 1/2011 | | |
| WO | WO-2011097355 A2 | 8/2011 | | |
| WO | WO-2011154942 A2 | 12/2011 | | |
| WO | WO-2012004679 A2 | 1/2012 | | |
| WO | WO-2012019052 A2 | 2/2012 | | |
| WO | WO-2012038550 A1 | 3/2012 | | |
| WO | WO-2012040865 A1 | 4/2012 | | |
| WO | WO-2012063228 A1 | 5/2012 | | |
| WO | WO-2012095159 A2 | 7/2012 | | |
| WO | WO-2012106354 A1 | 8/2012 | | |
| WO | WO-2012167095 A2 | 12/2012 | | |
| WO | WO-2012177942 A2 | 12/2012 | | |
| WO | WO-2013095816 A1 | 6/2013 | | |
| WO | WO-2013128436 A1 | 9/2013 | | |
| WO | WO-2013130641 A1 | 9/2013 | | |
| WO | WO-2013175468 A2 | 11/2013 | | |
| WO | WO-2014089424 A1 | 6/2014 | | |
| WO | WO-2014145399 A1 | 9/2014 | | |
| WO | WO-2014178869 A1 | 11/2014 | | |
| WO | WO-2014189509 A1 | 11/2014 | | |
| WO | WO-2014190329 A1 | 11/2014 | | |
| WO | WO-2014210600 A2 | 12/2014 | | |
| WO | WO-2015052629 A1 | 4/2015 | | |
| WO | WO-2015132668 A1 | 9/2015 | | |
| WO | WO-2016025894 A1 | 2/2016 | | |
| WO | WO-2016040526 A1 | 3/2016 | | |
| WO | WO-2018035118 A1 | 2/2018 | | |
| WO | WO-2018071540 A1 | 4/2018 | | |
| WO | WO-2018170424 A1 | 9/2018 | | |
| WO | WO-2020117842 A1 | 6/2020 | | |
| WO | WO-2020252200 A1 | 12/2020 | | |
| WO | WO-2022126249 A1 * | 6/2022 | | A61F 2/2466 |
| WO | WO-2022172108 A1 * | 8/2022 | | A61B 17/0487 |
| WO | WO-2022178042 A1 * | 8/2022 | | A61B 17/00234 |
| WO | WO-2023069494 A1 * | 4/2023 | | A61F 2/24 |
| WO | WO-2023228098 A1 * | 11/2023 | | A61B 17/0401 |

OTHER PUBLICATIONS

Extended European Search Report for European Application No. 11815347.7, mailed Mar. 14, 2016, 10 Pages.

Extended European Search Report for European Application No. 12793292.9, mailed Dec. 1, 2014, 6 Pages.

Extended European Search Report for European Application No. 13755441.6, mailed Mar. 1, 2016, 12 Pages.

Extended European Search Report for European Application No. 13860442.6, mailed Aug. 11, 2016, 7 pages.

Extended European Search Report for European Application No. 13885021.9, mailed Jan. 3, 2017, 8 Pages.

Extended European Search Report for European Application No. 14762806.9, mailed Jul. 29, 2016, 7 Pages.

Extended European Search Report for European Application No. 14801009.3, mailed Dec. 5, 2016, 8 Pages.

Extended European Search Report for European Application No. 14817662.1, mailed Jan. 23, 2017, 7 Pages.

Extended European Search Report for European Application No. 17155803.4, mailed Aug. 9, 2017, 10 Pages.

Extended European Search Report for European Application No. 17835256.3, mailed Feb. 12, 2020, 9 Pages.

Extended European Search Report for European Application No. 17841988.3, mailed Dec. 16, 2019, 8 Pages.

Extended European Search Report for European Application No. 17860901.2, mailed Jun. 5, 2020, 06 Pages.

Extended European Search Report for European Application No. 18768197.8, mailed Oct. 19, 2020, 7 Pages.

Extended European Search Report for European Application No. 19151726.7, mailed Jul. 22, 2019, 9 Pages.

Extended European Search Report for European Application No. 19170261.2, mailed Aug. 5, 2019, 9 pages.

Extended European Search Report for European Application No. 19893113.1, mailed Nov. 17, 2022, 7 Pages.

Extended European Search Report for European Application No. 20206790.6, mailed Dec. 7, 2020, 9 Pages.

Extended European Search Report for European Application No. 20209605.3, mailed Mar. 9, 2021, 7 pages.

Extended European Search Report for European Application No. 20823198.5, mailed May 15, 2023, 15 Pages.

Extended European Search Report for European Application No. 20823682.8, mailed Apr. 14, 2023, 10 Pages.

Extended European Search Report for European Application No. 20841346.8, mailed Jul. 21, 2023, 9 Pages.

International Preliminary Report on Patentability for International Application No. PCT/IL2022/050868, mailed Feb. 22, 2024, 11 Pages.

International Preliminary Report on Patentability for International Application No. PCT/US2011/046659, mailed Feb. 14, 2013, 9 Pages.

International Preliminary Report on Patentability for International Application No. PCT/US2012/040481, mailed Dec. 12, 2013, 8 Pages.

(56) References Cited

OTHER PUBLICATIONS

International Preliminary Report on Patentability for International Application No. PCT/US2013/028065, mailed Sep. 12, 2014, 09 Pages.
International Preliminary Report on Patentability for International Application No. PCT/US2013/042275, mailed Dec. 3, 2015, 12 Pages.
International Preliminary Report on Patentability for International Application No. PCT/US2013/073552, mailed Jun. 18, 2015, 8 Pages.
International Preliminary Report on Patentability for International Application No. PCT/US2014/030163, mailed Sep. 24, 2015, 9 Pages.
International Preliminary Report on Patentability for International Application No. PCT/US2014/039454, mailed Dec. 3, 2015, 10 Pages.
International Preliminary Report on Patentability for International Application No. PCT/US2014/044920, mailed Jan. 7, 2016, 12 Pages.
International Preliminary Report on Patentability for International Application No. PCT/US2017/044129, mailed Feb. 7, 2019, 8 Pages.
International Preliminary Report on Patentability for International Application No. PCT/US2017/046933, mailed Feb. 28, 2019, 8 Pages.
International Preliminary Report on Patentability for International Application No. PCT/US2017/056138, mailed Apr. 25, 2019, 5 Pages.
International Preliminary Report on Patentability for International Application No. PCT/US2018/022910, mailed Sep. 26, 2019, 6 Pages.
International Preliminary Report on Patentability for International Application No. PCT/US2019/064289, mailed Jun. 17, 2021, 7 Pages.
International Preliminary Report on Patentability for International Application No. PCT/US2020/037294, mailed Dec. 23, 2021, 7 Pages.
International Preliminary Report on Patentability for International Application No. PCT/US2020/037296, mailed Dec. 23, 2021, 7 Pages.
International Preliminary Report on Patentability for International Application No. PCT/US2020/042201, mailed Jan. 27, 2022, 6 Pages.
International Preliminary Report on Patentability for International Application No. PCT/US2021/071467, mailed Mar. 30, 2023, 11 Pages.
International Preliminary Report on Patentability for International Application No. PCT/US2021/071468, mailed Mar. 30, 2023, 7 Pages.
International Search Report & Written Opinion dated Jul. 24, 2024 in Int'l PCT Patent Appl. Serial No. PCT/US2024/019797.
International Search Report and Written Opinion for International Application No. PCT/IL2023/050527, mailed Aug. 8, 2023, 14 Pages.
International Search Report and Written Opinion for International Application No. PCT/US2011/046659, mailed Jun. 4, 2012, 13 Pages.
International Search Report and Written Opinion for International Application No. PCT/US2012/040481, mailed Dec. 6, 2012, 12 Pages.
International Search Report and Written Opinion for International Application No. PCT/US2013/028065, mailed Jun. 27, 2013, 11 Pages.
International Search Report and Written Opinion for International Application No. PCT/US2013/042275, mailed Feb. 20, 2014, 18 Pages.
International Search Report and Written Opinion for International Application No. PCT/US2013/058102, mailed Apr. 21, 2014, 10 Pages.

International Search Report and Written Opinion for International Application No. PCT/US2013/073552, mailed Mar. 6, 2014, 10 Pages.
International Search Report and Written Opinion for International Application No. PCT/US2014/030163, mailed Aug. 27, 2014, 10 Pages.
International Search Report and Written Opinion for International Application No. PCT/US2014/039454, mailed Oct. 22, 2014, 11 Pages.
International Search Report and Written Opinion for International Application No. PCT/US2014/044920, mailed Dec. 24, 2014, 15 Pages.
International Search Report and Written Opinion for International Application No. PCT/US2017/044129, mailed Sep. 27, 2017, 9 Pages.
International Search Report and Written Opinion for International Application No. PCT/US2017/046933, mailed Dec. 21, 2017, 11 Pages.
International Search Report and Written Opinion for International Application No. PCT/US2017/056138, mailed Jan. 8, 2018 , 6 Pages.
International Search Report and Written Opinion for International Application No. PCT/US2018/022910, mailed May 23, 2018, 7 Pages.
International Search Report and Written Opinion for International Application No. PCT/US2019/064289, mailed Feb. 5, 2020, 8 Pages.
International Search Report and Written Opinion for International Application No. PCT/US2020/037294, mailed Aug. 28, 2020, 8 Pages.
International Search Report and Written Opinion for International Application No. PCT/US2020/037296, mailed Sep. 10, 2020, 8 Pages.
International Search Report and Written Opinion for International Application No. PCT/US2020/042201, mailed Oct. 9, 2020, 7 Pages.
International Search Report and Written Opinion for International Application No. PCT/US2021/071467, mailed Jan. 14, 2022, 12 Pages.
International Search Report and Written Opinion for International Application No. PCT/US2021/071468, mailed Jan. 19, 2022, 8 Pages.
Lendlein et al., "Biodegradable, Elastic Shape-Memory Polymers for Potential Biomedical Applications," Science, May 31, 2002, vol. 296, pp. 1673-1676.
Partial Supplementary European Search Report for European Application No. 11815347.7, mailed Nov. 16, 2015, 06 Pages.
Partial Supplementary European Search Report for European Application No. 13755441.6, mailed Nov. 3, 2015, 7 Pages.
EP Extended Search Report dated May 23, 2025, in EP Patent Application Serial No. 22855660.1.
Extended European Search Report for European Application No. 21870447.6, mailed Nov. 11, 2024, 9 Pages.
Extended European Search Report for European Application No. 24215515.8, mailed Feb. 11, 2025—11 Pages.
Extended European Search Report for European Application No. 24219902.4, mailed Mar. 26, 2025—9 Pages.
Mitral Valve Repair Annuloplasty Rings: Surgeon Q&A with Dr. Steve Bolling], YouTube.com, Posted: Oct. 10, 2017[online], site visited: [Apr. 29, 2025], URL:https://www.youtube.com/watch?v=Pq4SE_iVbf0. (Year: 2021).
[Valcare Medical Announces First-in-Human Transseptal Implant of the Amend™ Annuloplasty Ring for Mitral Valve Repair], techwald. com, by [Herzliya, Israel], Published: [Jan. 27, 2021] [online], site visited: [Apr. 29, 2025], URL:https://www.techwald.com/valcare-medical-announces-first-in-human-transseptal-implant-of-the-amend-annuloplasty-ring-for-mitral-valve-repair/ (Year: 2021)].

* cited by examiner

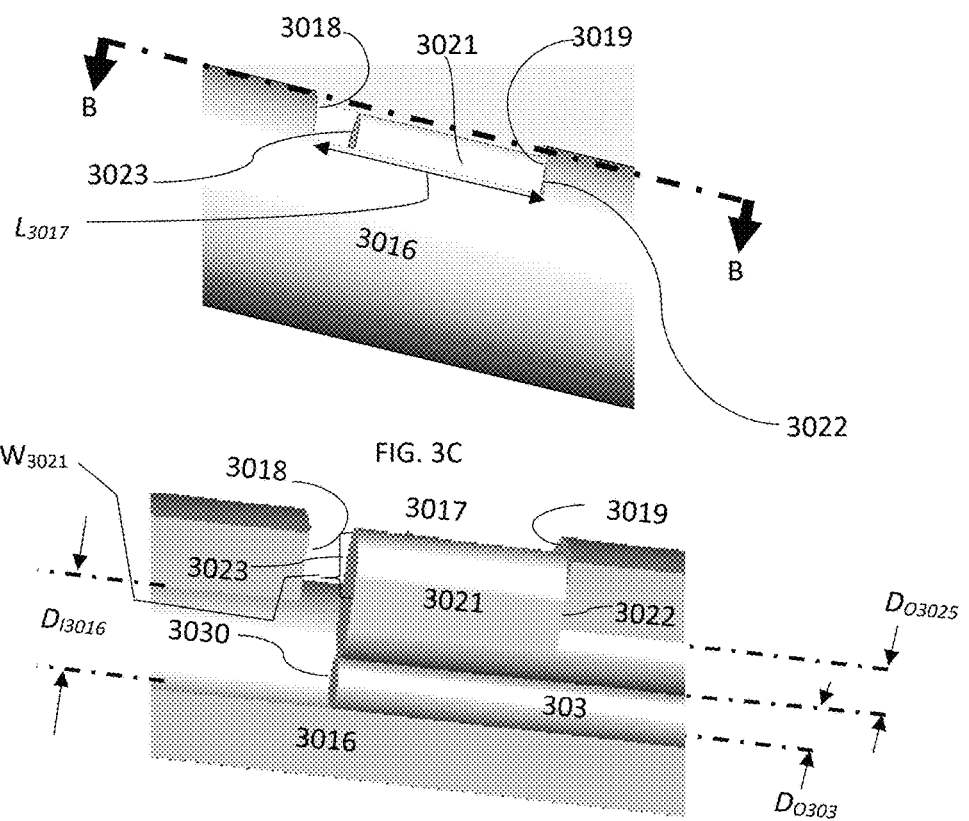
FIG. 3C
FIG. 3D
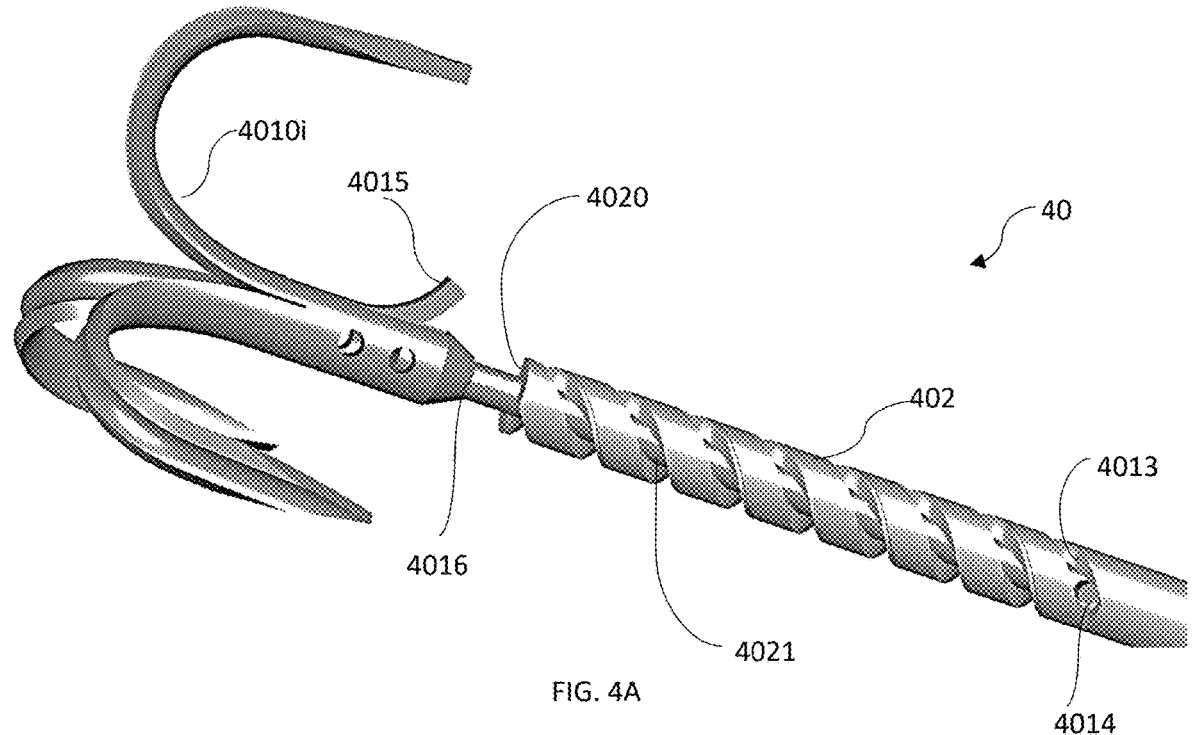
FIG. 4A

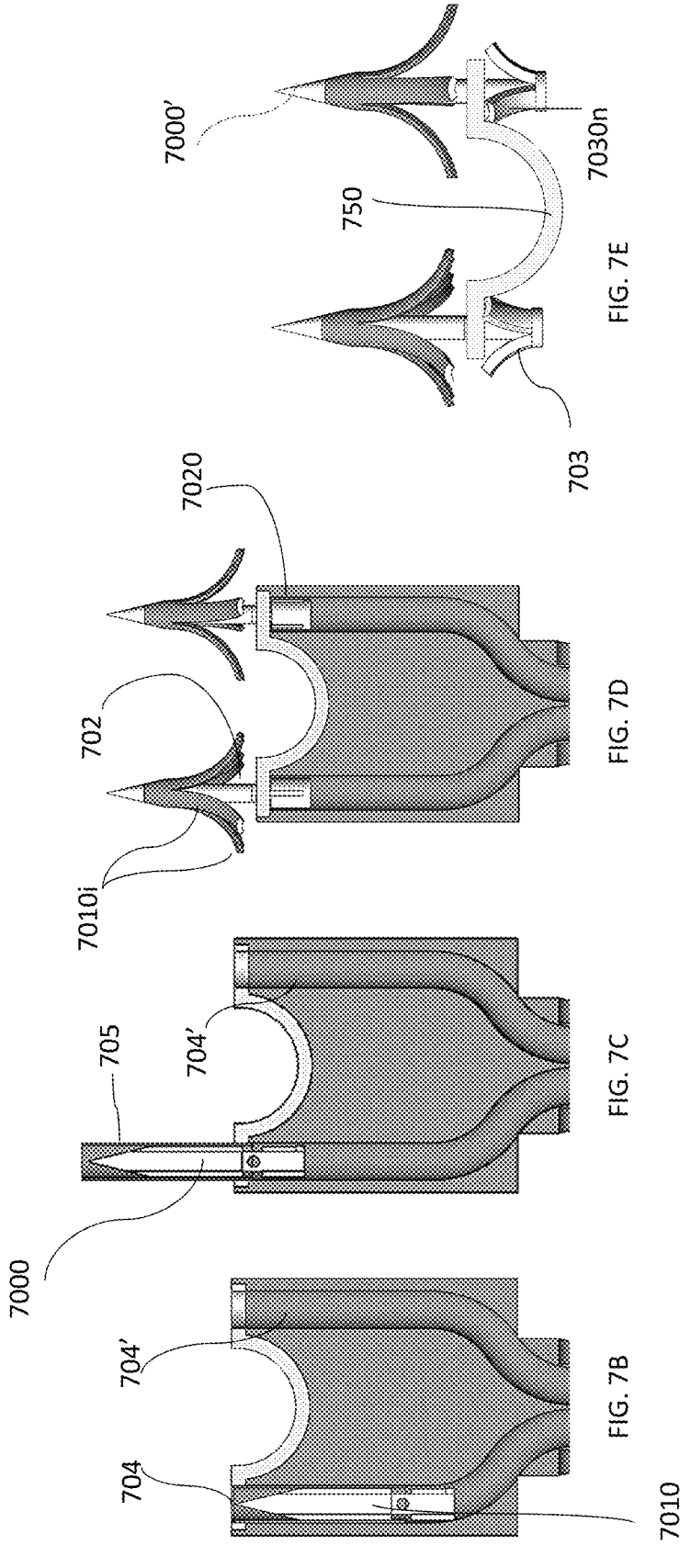

Retrieve

SYSTEMS AND METHODS FOR TARGET/ARTICLE BRIDGING ENGAGEMENT AND ANCHORING

BACKGROUND

The present disclosure is directed to system and methods for bridging a gap between an article or a portion thereof and a target, and anchoring the article or its portion to the target. Specifically, the disclosure is directed to methods and systems for use in bridging the gap between an article or a portion thereof and a target, engaging the target, and anchoring the article or its portion to the target.

There are various circumstances in the medical field where bridging the gap between an implanted article and a target may be required and/or desired, as a stand-alone procedure, or as a part of other procedures, not necessarily as a method of treatment of underlying pathological condition.

Moreover, the ability to bridge the gap between the particular article and the target may be desirably done by minimally invasive means, such as, for example, trans-apical and trans-septal procedures to reduce post procedure recovery time and complications.

An example for such a need is in the process of repairing structural heart valves, such as the mitral valve, the tricuspid valve, the aortic valve and the pulmonary valves before, during or after annuloplasty ring is put into place.

The proposed technology aims to address the shortcomings of the current systems and methods.

SUMMARY

In an exemplary implementation, provided herein is a system for bridging a gap between an article or a portion thereof and a target, and anchoring the article or its portion to the target, the system comprising: an elongated delivery catheter having a distal end; and a bridging and anchoring construction, operable to selectably translate in a distal and a proximal direction relative to the distal end of the elongated delivery catheter, the bridging and anchoring construction slidably coupled to the elongated delivery catheter, wherein the bridging and anchoring construction is operable to engage the target following the distal translation spanning the gap between the article or its portion and the target; eliminating the gap following the proximal translation; and anchoring the article or its portion to the target.

In another exemplary implementation, provided herein is a method for bridging a gap between an article or a portion thereof and a target, and anchoring the article or its portion to the target, the method implementable in a system comprising an elongated delivery catheter having a distal end; and a bridging and anchoring construction, operable to selectably translate in a distal and a proximal direction relative to the distal end of the elongated delivery catheter, the bridging and anchoring construction slidably coupled to the elongated delivery catheter, wherein the bridging and anchoring construction is operable to engage the target following a distal translation spanning the gap between the article or its portion and the target; eliminating the gap following a proximal translation; and anchoring the article or its portion to the target, the method comprising: inserting the delivery catheter; partially engaging the article or its portion; translating the bridging and anchoring construction in a distal direction relative to the delivery catheter's distal end over the gap; using the bridging and anchoring construction engaging the target; translating the bridging and anchoring construction in a proximal direction relative to the delivery catheter's distal end to the point where the target abuts the article or its portion; and using the bridging and anchoring construction anchoring the article or its portion to the target.

In yet another embodiment, provided herein is a use of a gap bridging and anchoring system in the process of bridging the gap between an article or a portion thereof and a target, and anchoring the article or its portion to the target, the system comprising: an elongated delivery catheter having a distal end; and a bridging and anchoring construction, operable to selectably translate in a distal and a proximal direction relative to the distal end of the elongated delivery catheter, the bridging and anchoring construction slidably coupled to the elongated delivery catheter, wherein the bridging and anchoring construction is operable to engage the target following a distal translation spanning the gap between the article or its portion and the target; eliminating the gap following a proximal translation; and anchoring the article or its portion to the target.

BRIEF DESCRIPTION OF THE DRAWINGS

The method implementable using the gap bridging, engagement and anchoring systems disclosed herein will become apparent from the following detailed description when read in conjunction with the figures, which are exemplary, not limiting, and in which:

FIG. 4A, illustrating a third exemplary implementation of the bridging and anchoring construction, post engagement of the piercing tip, with FIG. 4B, illustrating an exploded view thereof, with unstrained foreshaft in an anchoring configuration;

3

Figures 1A, 1B, 1C, 1D, 1E:
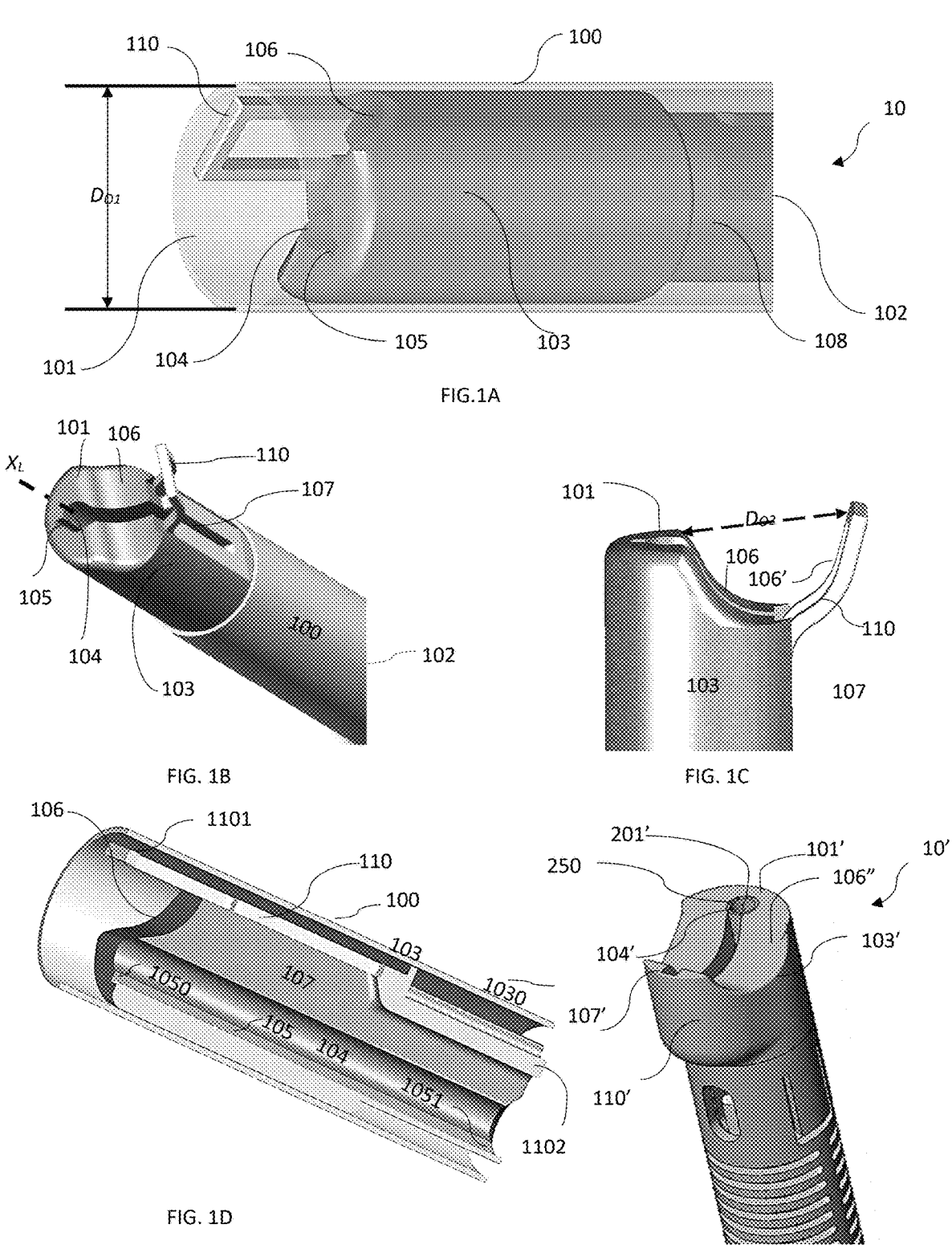
FIG. 1A is a schematic of a delivery catheter's distal end, FIG. 1B illustrating the delivery catheter in engagement configuration, with FIG. 1C illustrating enlarged section of the distal end of the delivery catheter illustrated in FIG. 1B, with FIG. 1D illustrating a Y-Z cross section of the delivery catheter illustrated in FIG. 1A, and FIG. 1E illustrating another schematic of a delivery catheter's distal end.

While the disclosure of the system for bridging a gap between an article or a portion thereof and a target, and anchoring the article or its portion to the target, is amenable to various modifications and alternative forms, specifics thereof have been shown by way of example in the drawings and will be further described in detail below. It should be understood, however, that the intention is not to limit the disclosure to the particular exemplary implementations illustrated. On the contrary, the intention is to cover all obvious modifications, equivalents, and alternatives.

DETAILED DESCRIPTION

Provided herein are exemplary implementations of methods and systems for use in bridging the gap between an article or a portion thereof and a target, engaging the target, and anchoring the article or its portion to the target. The target can be, for example: a pulmonary valve, a mitral valve, a tricuspid valve, an aortic valve and like valves and annuli requiring repair by implanting support structures. Similarly, the article can be an annuloplasty ring or a portion thereof, adapted, sized and configured to be anchored to the target.

Furthermore, in the context of the disclosure, the term 'article, or its' portion (whether toroidal or not), does not necessarily mean a ring defining a single plane, but rather encompasses other planes, for example a saddle-shaped ring. Likewise, the term "its' (first, second) portion" means, in the context of the disclosure, any part of the article operable to be adjoined to form the full article (e.g., annuloplasty ring).

Definitions

The term "coupled", including its various forms such as "operably coupling", "coupling" or "couplable", refers to and comprises any direct or indirect, structural coupling, connection or attachment, or adaptation or capability for such a direct or indirect structural or operational coupling, connection or attachment, including integrally formed components and components which are coupled via or through another component or by the forming process. Indirect coupling may involve coupling through an intermediary member or adhesive, or abutting and otherwise resting against, whether frictionally or by separate means without any physical connection.

In addition, for the purposes of the present disclosure, directional or positional terms such as "top", "bottom", "upper," "lower," "side," "front," "frontal," "forward," "rear," "anterior", "posterior", "proximal", "distal", "rearward," "back," "trailing," "leading," "above," "below," "left," "right," "radial," "vertical," "upward," "downward," "outer," "inner," "exterior," "interior," "intermediate,", "apical", "basal", etc., are merely used for convenience in describing the various exemplary implementations of the present disclosure and provide with an orientation of the various elements.

Likewise, the term "engage" and various forms thereof, when used with reference to an engaging element, for example in the engagement of proximal section 2012 of foreshaft 2016 with distal section 2021 of pushtube 202, refers in an exemplary implementation to the application of any forces that tend to hold proximal section 2012 and distal section 2021 together against inadvertent or undesired separating forces (e.g., such as may be introduced during manipulation of pushrod 202). It is to be understood, however, that engagement does not in all cases require the interlocking connection that is maintained against every conceivable type or magnitude of separating force. Further, the term "engaging element" refers in another exemplary implementation to one or a plurality of coupled components, at least one of which is configured for releasably engaging another element. Thus, this term encompasses both single part engaging elements and multi-part-assemblies, such as bridging and anchoring construction 20, 30, 40.

The terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., lance-member(s) 2014j includes one or more lance member).

Reference throughout the specification to "one exemplary implementation", "another exemplary implementation", "an exemplary implementation", and so forth, means that a particular element (e.g., step, feature, structure, and/or characteristic) described in connection with the exemplary implementation is included in at least one exemplary implementation described herein, and may or may not be present in other exemplary implementations. In addition, it is to be understood that the described elements may be combined in any suitable manner in the various exemplary implementations.

In the context of the disclosure, the term "operable" means the system and/or the device, or a certain element or step is fully functional, sized, adapted and calibrated, comprises elements for, and meets applicable operability requirements to perform a recited function when activated, coupled, implemented, actuated, effected, or realized. In relation to systems, the term "operable" means the system is fully functional and calibrated, having the necessary elements, as well as the mechanisms for, and meets applicable operability requirements to perform a recited function when executed by a user.

The term "abut" refers in the context of the disclosure, to items that are in direct physical contact with each other, although the items may not be attached, secured, fused, glued, sewn, or welded together.

A more complete understanding of the methods and systems for use in bridging the gap between an article or a portion thereof and a target, engaging the target, and anchoring the article or its portion to the target, can be obtained by reference to the accompanying drawings. These figures (also referred to herein as "FIG.") are merely schematic representations based on convenience and the ease of demonstrating the present disclosure, and are, therefore, not intended to indicate relative size, scale and dimensions of the devices or components thereof, and/or to define or limit the scope of the exemplary implementations. Although specific terms are used in the following description for the sake of clarity, these terms are intended to refer only to the particular structure of the exemplary implementations selected for illustration in the drawings, and are not intended to define or limit the scope of the disclosure. In the drawings and the following description below, it is to be understood that like numeric designations refer to components of like function.

Figure 5B:
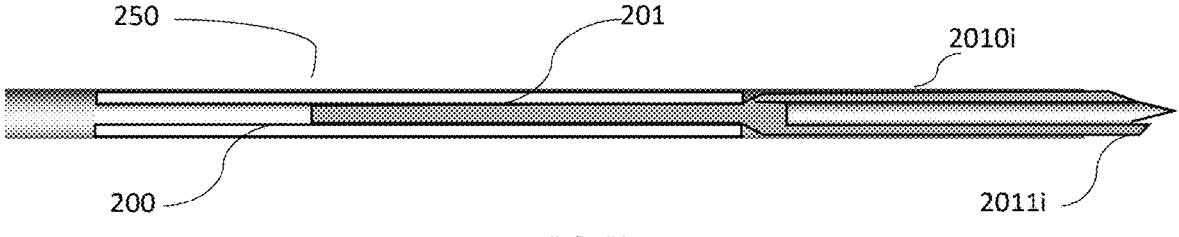

In the context of the disclosure, the term "strained" as used to describe the strained foreshaft (e.g., 201 see e.g., FIG. 2A) means that the foreshaft is maintained under an extrinsic tensile strain. An "extrinsic strain" as used herein refers to a tensile strain that is applied to the foreshaft by the sheath (or an external force exerted by another member), rather than a tensile strain developed within the strained foreshaft. In other words, in the unstrained position (see e.g., FIG. 2C), the foreshaft, formed of a resilient material (e.g., nitinol, stainless steel and the like) curls, and the insertion into sheath 200, or jacket 250 (see e.g., FIG. 5B) causes the tensile stress to form the strain imposed on the foreshaft or piercing tip's piercing lances.

Turning now to FIGS. 1A-5B, illustrating exemplary implementation of the systems for use in bridging the gap between an article or a portion thereof and a target, engaging the target, and anchoring the article or its portion to the target. As illustrated, in FIG. 1A-2D, the system comprises: elongated delivery catheter 10, 10' having distal end 101, 101' (see e.g., FIGS. 1A, 1E); and bridging and anchoring construction (see e.g., 20, 30, 40 FIGS. 2A, 3A, 4A), each bridging and anchoring construction 20, 30, 40 operable to selectably translate in a distal and a proximal direction relative to distal end 101 of elongated delivery catheter 10, 10', each of bridging and anchoring construction 20, 30, 40 slidably coupled to elongated delivery catheter 10, 10' wherein each bridging and anchoring construction 20, 30, 40 is operable to engage target 900 (see e.g., FIG. 4B, 6A) following distal translation spanning the gap between article 800 (see e.g., FIGS. 2C, 6A, 6B) or its portion and target 900; eliminating the gap following proximal translation; and anchoring article 800 or its portion to the target 900.

Figures 9A, 9B, 9C, 9D, 9E, 9F, 9G:
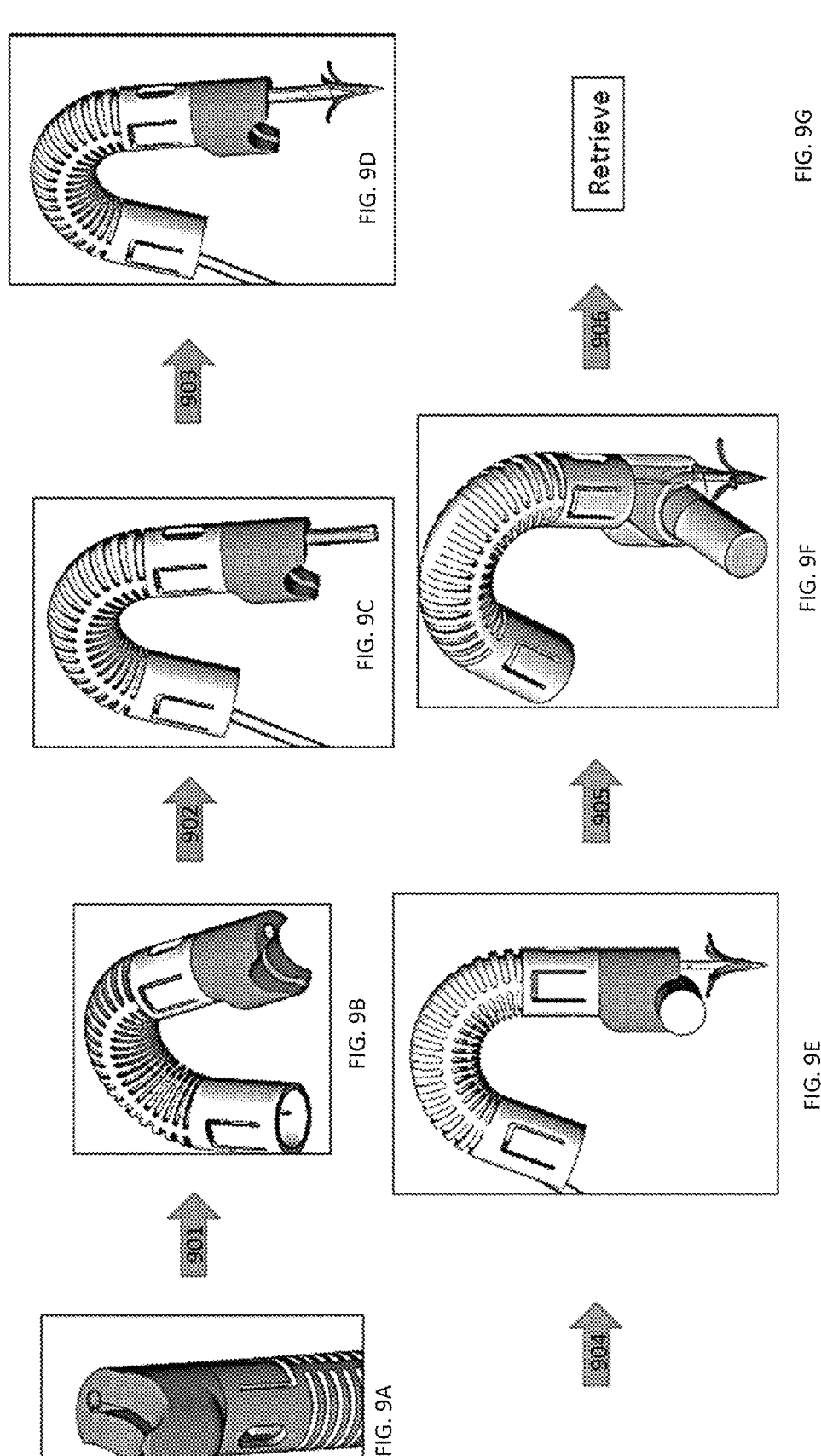
FIGS. 9A-9G, illustrate the use of delivery catheter as illustrated in FIG. 1E, to deliver the bridging and anchoring constructs disclosed.

As further illustrated in FIG. 1A-1E, delivery catheter 10, is operable to transition between an insertion configuration as illustrated in FIGS. 1A, and ID and engagement configuration illustrated e.g., in FIGS. 1B and 1C, wherein distal end 101 is contoured 106 to abut at least portion of article 800 or its portion's surface (see e.g., for elongated catheter 10', FIG. 9F) in its engagement configuration (FIGS. 1B and 1C), elongated delivery catheter 10 further comprises: cylindrical sleeve 100, operable to slidably translate in proximal direction; cylindrical housing 103, defining through bore 104, sized to accommodate jacket 250 housing each of bridging and anchoring construction 20, 30, 40, cylindrical housing 103 having distal end 101 with arcuate cross section 106 (see e.g., FIG. 1D) sized to abut between about 1.0 radians, and about 4.5 radians of at least portion of article 800 (see e.g., FIGS. 2C, 9F) or its portion's surface. It is noted that surface 106 in distal end 101 of cylindrical housing 103 does not need to be specifically arcuate, but rather, in certain exemplary implementations, have a surface that is complementary to a predetermined portion of article 800 configured to be manipulated to assist in locating article 800 relative to target 900 (see e.g., FIG. 6A, and 9A-9F). Also illustrated in FIGS. 1A-1D, is expander 110, operable to transition between strained position within sleeve 100 and unstrained position outside sleeve 100, wherein, in its unstrained position (FIGS. 1B and 1C), distal portion 1101 (see e.g., FIG. 1D) of expander 110 forms complimentary arcuate cross section 106' to arcuate cross section 106 of distal end 101 of cylindrical housing 103. Similarly, it is noted that surface 106, 106' formed by distal end 101 of cylindrical housing 103, and expander 110 in its unstrained configuration does not need to be specifically arcuate, but rather form a surface that is complementary to a predetermined portion of article 800 configured to be manipulated to assist in locating article 800 relative to target 900.

Also illustrated in FIGS. 1A, 1B, and 1D, is groove 105 configured to receive and accommodate each of protruding tab 2015, 3015, and 4015 of bridging and anchoring construction 20, 30, 40 respectively. Similarly, and as illustrated in FIG. 1B, slit 107 formed in cylindrical housing 103, is configured to accommodate each of foreshaft 201, 301, and 401 of bridging and anchoring construction 20, 30, 40 respectively is they transition from their strained to unstrained configuration as disclosed herein. As further illustrated in FIG. 1D, expander 110 having distal end 1101 and proximal end 1102, can be engaged, in an exemplary implementation, in channel 1030 within cylindrical housing 103 and be extrinsically strained by sleeve 100, such that upon proximal translation (pulling e.g.,) of sleeve 100 beyond the interface of arcuate surface 106 with expander 110, expander 110 will transition to its unstrained configuration. Likewise, as illustrated in FIG. 1D, (applying also to the exemplary implementation illustrated in FIG. 1E) groove 105, having distal end 1050 and proximal end 1051, is configured to accommodate protruding tab 2015, 3015, and 4015 of bridging and anchoring construction 20, 30, 40 respectively thus preventing each of bridging and anchoring construction 20, 30, 40 from radially rotating about longitudinal axis $X_L$ (see e.g., FIG. 3B) during the distal translation (pushing e.g.,) of each of bridging and anchoring construction 20, 30, 40.

In another exemplary implementation illustrated in FIG. 1E, elongated catheter 10' comprises: cylindrical housing 103', defining through bore 104', sized to accommodate each of bridging and anchoring construction 20, 30, 40, (e.g., jacket 250 accommodating each anchoring construction 20, 30, 40), cylindrical housing 103' having distal end 101' with arcuate cross section 106" sized to abut between about 1.0 radians, and about 4.5 radians of at least portion of article 800 (see e.g., FIGS. 2C, 9F) or its portion's surface. Also illustrated, is slit 107' formed in cylindrical housing 103', configured likewise to accommodate each of foreshaft 201, 301, and 401 of bridging and anchoring construction 20, 30, 40 respectively is they transition from their strained to unstrained configuration as disclosed herein (see e.g., FIG. 9F).

Figure 2A:
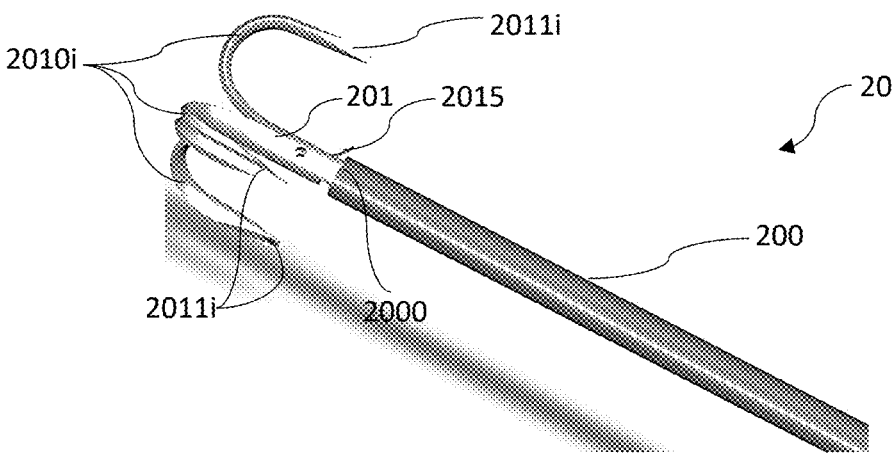
FIG. 2A, illustrating a first exemplary implementation of the bridging and anchoring construction, post engagement of the piercing tip, with FIG. 2B, illustrating an exploded view thereof, and FIG. 2C illustrating unstrained foreshaft in an anchoring configuration.
Figure 2B:
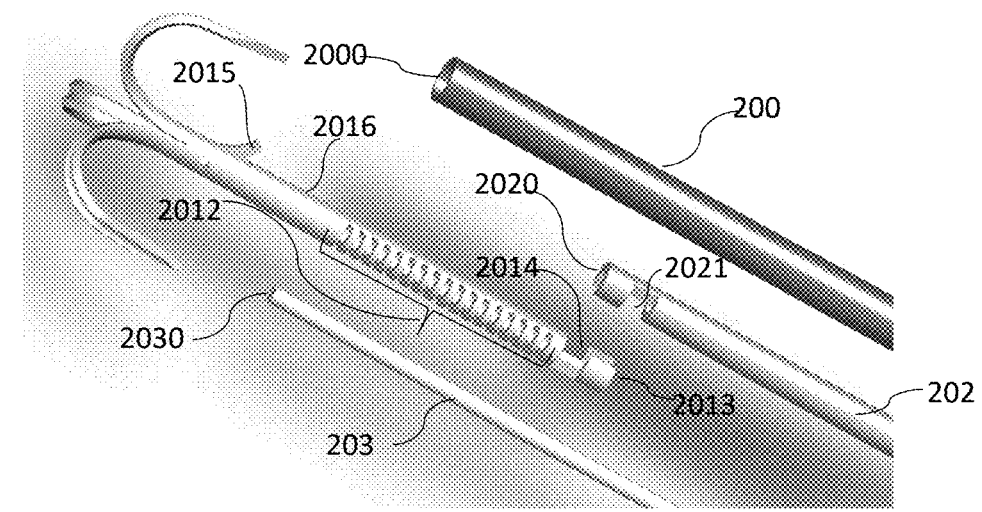
Figure 2C:
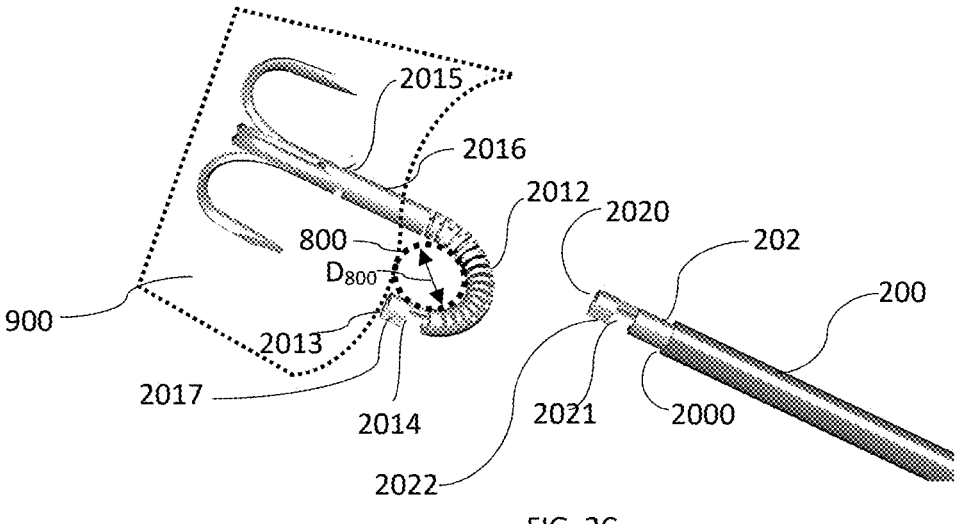

Turning now to FIGS. 2A-2C, illustrating first exemplary implementation of bridging and anchoring construction 20, following engagement of piercing tip 2010, with FIG. 2B, illustrating an exploded view thereof, and FIG. 2C illustrating unstrained foreshaft 201 in an anchoring configuration. As illustrated, bridging and anchoring construction 20 used in the methods disclosed for the uses described, can comprises in an exemplary implementation: jacket 250, (see e.g., FIGS. 5A, 5B), sheath 200; piercing tip 2010 comprised of plurality of lancing members 2010$i$, each i$^{th}$ piercing tip (e.g., between 3 and 5) 2010$i$ having sharpened tip end 2011$i$, configured to transition between strained position within jacket 250 and unstrained position outside jacket 250 upon distal translation of piercing tip 2010 outside of jacket 250. Also shown, is tubular (in other words, axially hollow) foreshaft 201 having proximal end 2016, tubular foreshaft 201 distally coupled to piercing tip 2010, whereby tubular foreshaft 201 comprises proximal region 2012 configured to transition between strained position (see e.g., FIG. 2A) when coupled to at least one of: coupling rod 203 inserted coaxially within tubular foreshaft 201, and sheath 200, and unstrained position (see e.g., FIG. 2C) following proximally translating at least one of (in other words, and/or): coupling rod 203 inserted coaxially within the tubular foreshaft, and sheath 200; proximal end 2013 forming portion of proximal region 2012, proximal end 2013 operable to form engagement section 2014 with T-line interrupted wall. In other words, the T-line interrupted wall has a T-shape cut into the wall with the leg extending from proximal end 2013 to some distance culminating with the cross bar. The T-line interrupted wall is adapted, sized and configured to receive and accommodate a complementary engagement portion (e.g., 2021). Thus, bridging and anchoring construction 20 further comprises pushtube 202, having proximal end 2020 operable to form engagement section 2021 with T-line interrupted wall, complementary to engagement section 2014 of tubular foreshaft 201, releasably coupled coaxially to proximal end 2013 of tubular foreshaft 201. Moreover, and as indicated coupling rod 203, when present, sized to be accommodated coaxially within pushtube 202, extending into tubular foreshaft 201 in distal direction beyond strained proximal region 2012, thus providing an alternative, or additional extrinsic strain on proximal region 2012, which can be slotted with slots distanced such that the unconstrained configuration will define a predetermined shape, for example, an arc having predetermined internal diameter $D_{800}$ as illustrated in FIG. 2C.

Figures 3A, 3B:
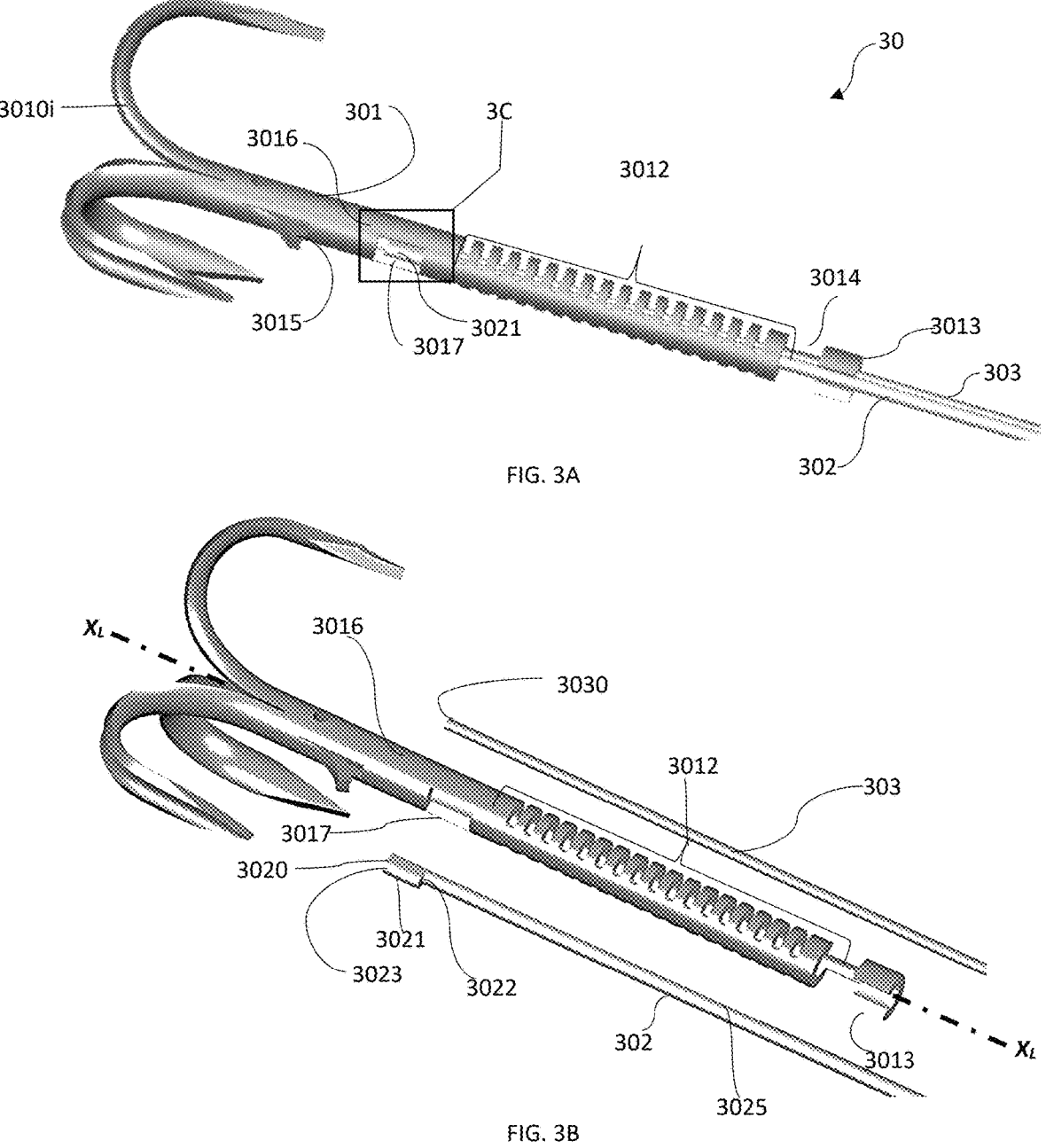
FIG. 3A, illustrating a second exemplary implementation of the bridging and anchoring construction, post engagement of the piercing tip, with FIG. 3B, illustrating an exploded view thereof, FIG. 3C illustrating the enlarged portion marked 3C in FIG. 3A, with FIG. 3D illustrating a Y-Z cross section of FIG. 3C along line B-B.

Another exemplary implementation of bridging and anchoring construction 30 is illustrated in FIGS. 3A-3D, where FIG. 3A, illustrates bridging and anchoring construction 30, post engagement of the piercing tip 3010, with FIG. 3B, illustrating an exploded view thereof, FIG. 3C illustrating the enlarged portion marked 3C in FIG. 3A, and FIG. 3D illustrating a Y-Z cross section of FIG. 3C along line B-B. As illustrated, bridging and anchoring construction 30 comprises: jacket 250 (see e.g., generally FIGS. 5A, 5B) optionally sheath 200 (see e.g., FIG. 2B); piercing tip 3010 comprised of plurality of lancing members 3010i each $i^{th}$ lancing member 3010i configured to transition between strained position within jacket 250 (see e.g., FIG. 5B) and unstrained position outside jacket 250 (see e.g., FIG. 3A). Similar to bridging and anchoring construction 20, bridging and anchoring construction 30 also comprises tubular foreshaft 301 having proximal end 3013, tubular foreshaft 301 distally coupled to piercing tip 3010, comprising proximal region 3012 configured to transition between strained position when coupled to pushrod 302 inserted coaxially within tubular foreshaft 301 and at least one of: coupling rod 303, and optionally sheath 200 (see e.g., FIG. 5B), and unstrained position following decoupling of pushrod 302 and proximal translation of coupling rod 303, and/or sheath 200. Tubular foreshaft 301 further defining radial opening 3017, defined in tubular foreshaft's 301 wall, radial opening 3017 defined distal to proximal region 3012, having proximal end 3019 (see e.g., FIG. 3C) and distal end 3018, radial opening 3017 being sized to accommodate distal portion 3021 of pushrod 302. Pushrod 302, with distal portion 3021 extending radially from pushrod's 302 distal end, wherein distal portion 3021 forms tab extending radially from pushrod 302 to distance W (see e.g., FIG. 3D), that is larger than radius ($D_{I3016}/2$) of internal diameter $D_{I3016}$ of tubular foreshaft 301 and smaller than internal diameter $D_{I3016}$ of tubular foreshaft 301 and wherein proximal portion 3025 (see e.g., FIG. 3B) of pushrod 302 has outer diameter $D_{O3025}$, that is not larger than radius ($D_{I3016}/2$) of internal diameter $D_{I3016}$ of tubular foreshaft 301 (see e.g., FIG. 3D). Also illustrated is coupling rod 303, which, when used in certain exemplary implementations, is sized to be accommodated coaxially within tubular foreshaft 301 extending in distal direction beyond the strained proximal region 3012. Coupling rod 302 is sized to have outer diameter $D_{O303}$ that is not larger than the ($D_{I3016}/2$) of internal diameter $D_{I3016}$ of tubular foreshaft 301.

Figures 4B, 5A:
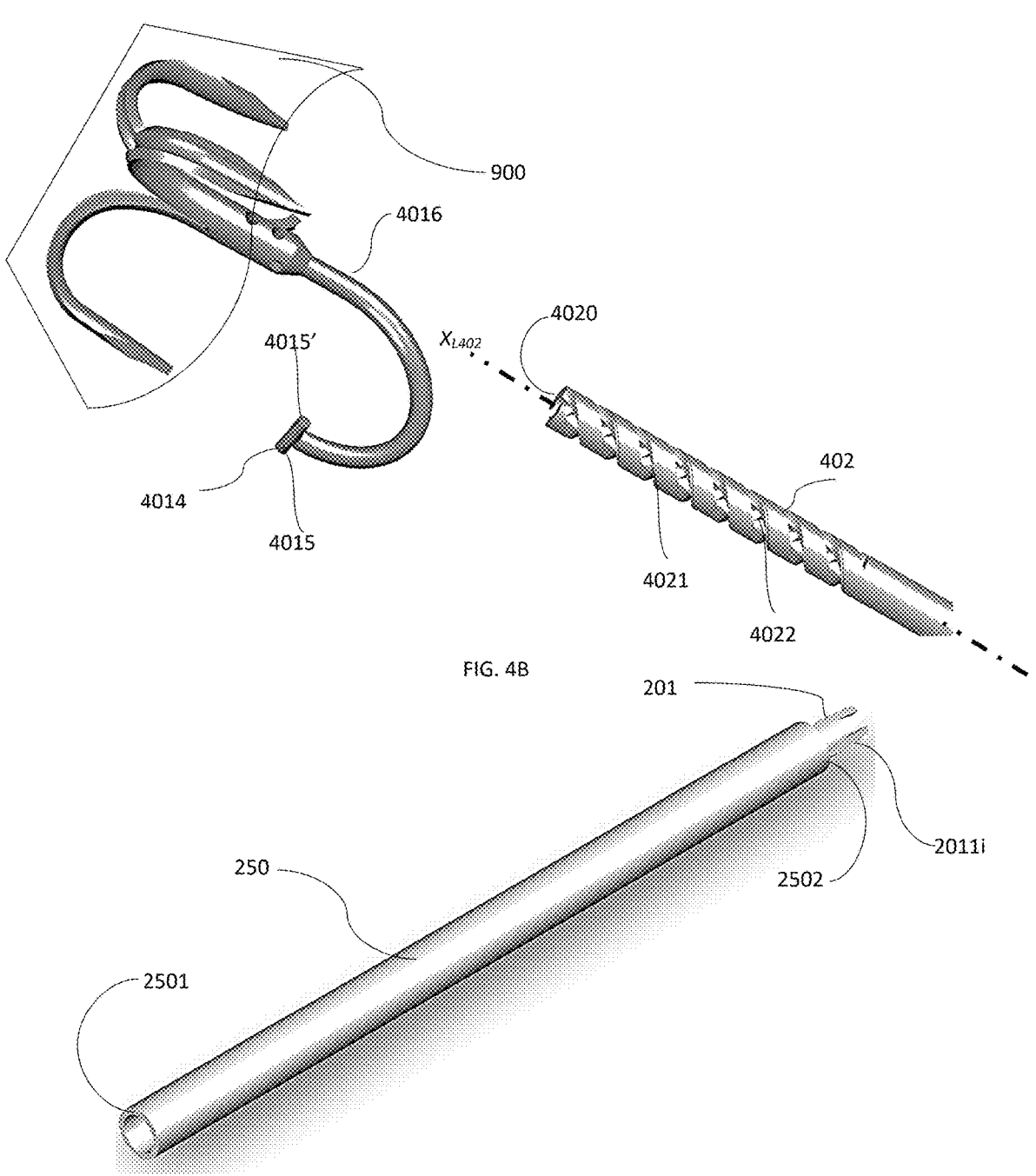
FIG. 5A illustrates an exemplary implementation of the bridging and anchoring construction, with FIG. 5B, illustrating a X-Z cross section thereof.
Figure 6A:
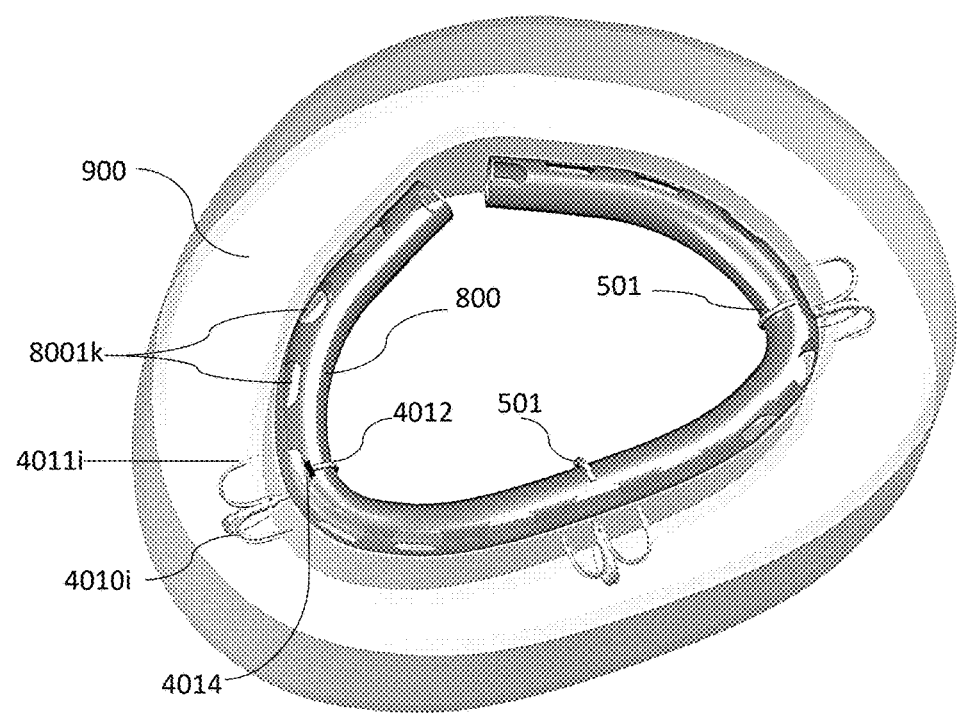
FIG. 6A, illustrating an anchored annuloplasty ring anchored to a structural heart valve; with FIG. 6B, illustrating an exemplary implementation using more than one type of anchor.
Figure 6B:
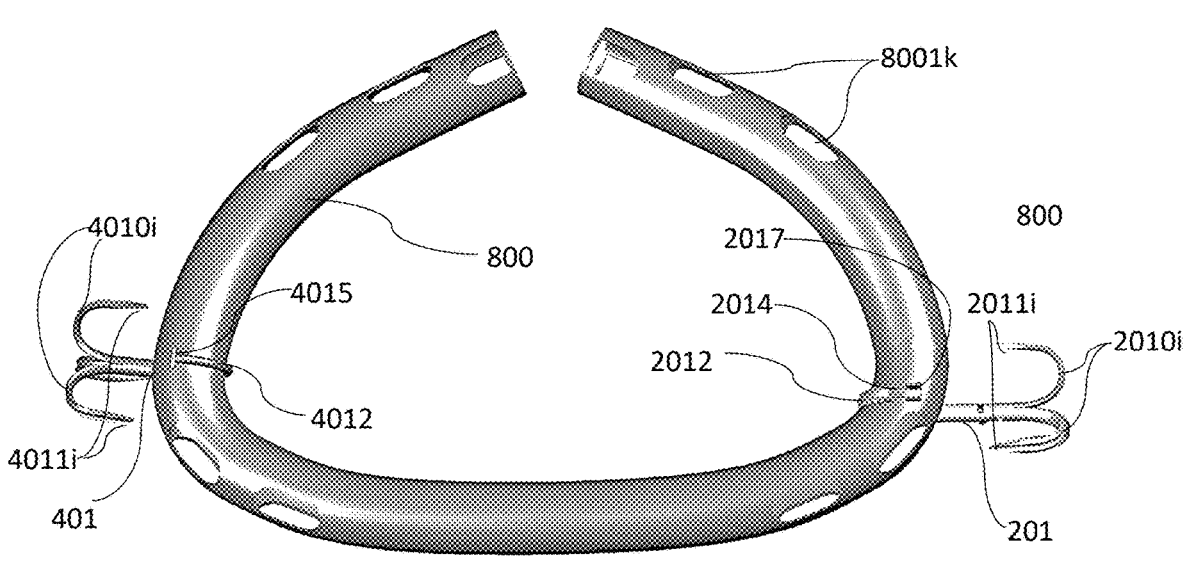

Yet another exemplary implementation of bridging and anchoring construction 40 is illustrated in FIGS. 4A and 4B, illustrating a third exemplary implementation of the bridging and anchoring construction 40, post engagement of the piercing tip 4010 (see e.g., FIG. 6B), with FIGS. 4B, illustrating an exploded view thereof, with unstrained foreshaft 401 in an anchoring configuration (see e.g., FIG. 6A). As illustrated in FIG. 4A, bridging and anchoring construction comprises: jacket 250; optionally sheath 200 (see e.g., FIG. 2B); piercing tip 4010 comprised of plurality of lancing members 4010i, each $i^{th}$ lancing member 4010i configured to transition between strained position within jacket 250 and unstrained position outside jacket 250. Also shown is pushtube 402, having distal portion 4021 defining helical wall channel 4022, helical wall channel 4022 (see e.g., FIG. 4B) having predetermined pitch (referring to the distance along longitudinal axis $X_{L402}$ to complete a 360° turn) configured to engage proximal portion 4013 of foreshaft 401. As illustrated in FIG. 4A, foreshaft 401 having distal end 4016 coupled to piercing tip 4010, and proximal portion 4013 with proximal end 4014 with pair of diametrically opposed pegs 4015, 4015' extending laterally from proximal end 4014 of foreshaft 401 wherein: pair of diametrically opposed pegs 4005, 4015' extending laterally are sized and configured to be accommodated in helical wall channel 4022 of pushtube 402; and proximal portion 4013 is configured to transition between strained position when engaged in pushtube 402 (see e.g., FIG. 4A) and unstrained position (see e.g., FIG. 4B) outside pushtube 402.

As indicated, the systems disclosed used as described, implement in certain exemplary implementations the methods provided. Accordingly, and in an exemplary implementation illustrated schematically in FIGS. 9A-9G, provided herein is a method for bridging a gap between an article or a portion thereof and a target, and anchoring the article or its portion to the target, the method implementable in a system comprising elongated delivery catheter 10, 10' having distal end 101 101'; and bridging and anchoring construction 20, 30, 40, operable to selectably translate in a distal and a proximal direction relative to distal end 101, 101' of elongated delivery catheter 10, 10' bridging and anchoring construction 20, 30, 40 slidably coupled to elongated delivery catheter 10, 10' wherein bridging and anchoring construction 20, 30, 40 is operable to engage target 900 following distal translation spanning gap between article 800 or its portion and target 900 (see e.g., FIG. 6A); eliminating the gap following proximal translation; and anchoring article 800 or its portion to target 900 (see e.g., FIGS. 6A, 6B), whereby the method comprises: inserting delivery catheter 10, 10'; partially engaging article 800 (901, FIGS. 9A, 9B) or its portion to delivery catheter 10, 10'; translating bridging and anchoring construction 20, 30, 40 in distal direction (902, FIGS. 9B, 9C) relative to delivery catheter's 10, 10' distal end 101, 101' over the gap; using bridging and anchoring construction 20, 30, 40, engaging target 900 (903, FIGS. 9C, 9D); translating bridging and anchoring construction 20, 30, 40 in proximal direction (pulling, (904, FIGS. 9D, 9E) relative to delivery catheter's 10, 10' distal end 101, 101' to a point where target 900 abuts article 800 (see e.g., FIG. 2C) or its portion; and using bridging and anchoring construction 20, 30, 40, anchoring (905, FIGS. 9E, 9F) article 800 or its portion to target 900 (see e.g., FIGS. 6A, 6B).

In the methods disclosed, the gap between the article or its portion and the target, is between about 0.01 mm and about 40 mm. In other words, the gap can be minimal and the use of the systems disclosed can be to permanently or temporarily anchor the article (e.g., an annuloplasty ring, see e.g., FIG. 6A) to the target, (for example, a mitral valve annulus, a tricuspid valve annulus, or a pulmonary valve annulus).

Furthermore, in another exemplary implementation, the step of transitioning delivery catheter 10 from insertion configuration (see e.g., FIG. 1A) to engagement configuration (see e.g., FIG. 1C), comprises retracting sleeve 100 in a proximal direction, causing expander 110 to transition to its unstrained position as illustrated in FIGS. 1B, and 1C, where cylindrical housing 103 having distal end 101 with arcuate cross section 106 (see e.g., FIG. 1D) sized to abut between about 1.0 radians, and about 4.5 radians of at least portion of article 800 (see e.g., FIG. 2C) or its portion's surface and expander 110, in its unstrained position (FIGS. 1B and 1C), distal portion 1101 (see e.g., FIG. 1D) of expander 110 forms complimentary arcuate cross section 106' to arcuate cross section 106 of distal end 101 of cylindrical housing 103.

Figures 8A, 8B, 8C, 8D, 8E:
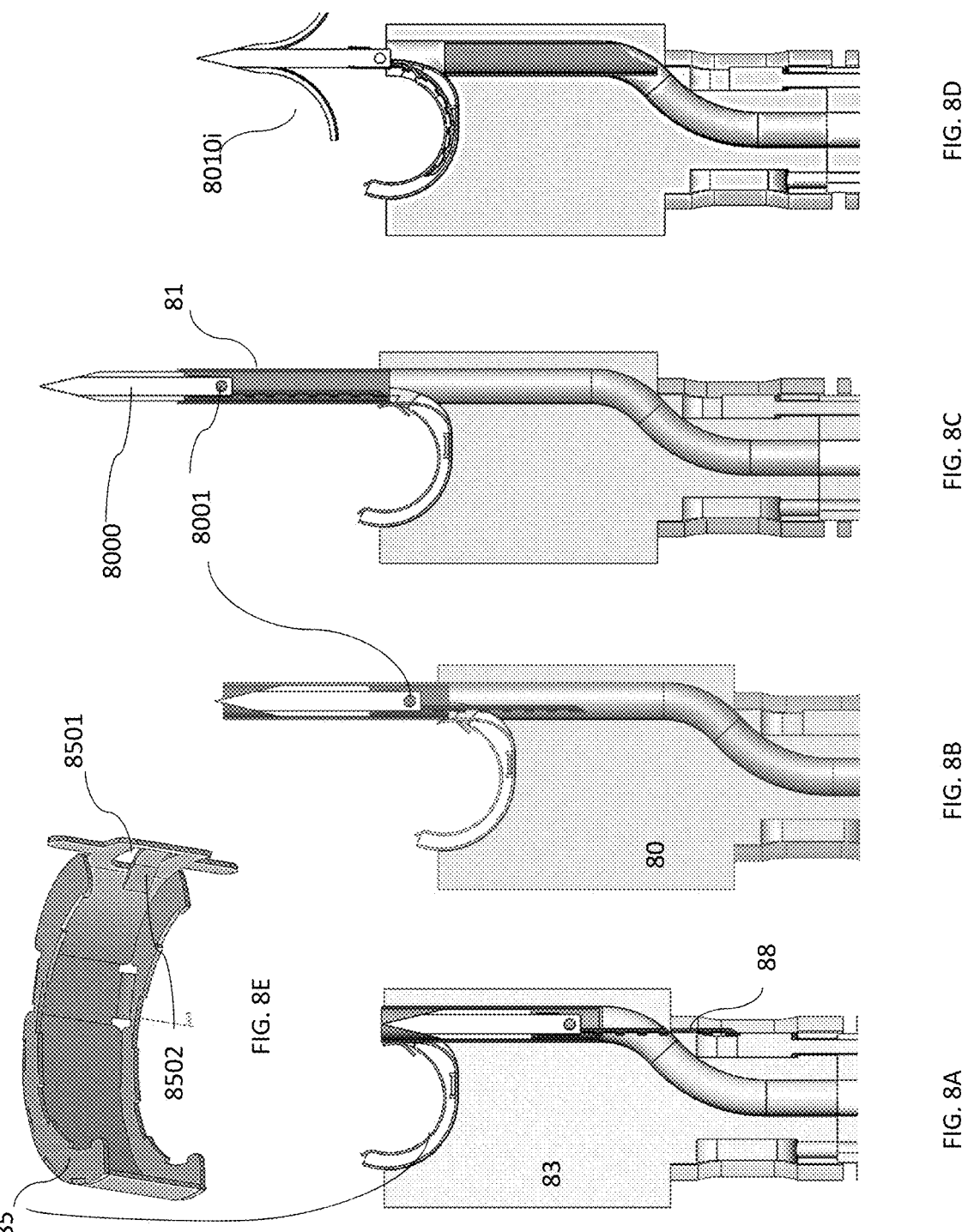
FIGS. 8A-8E, illustrates yet another exemplary implementation of the methods and systems disclosed.

Thereafter, in an exemplary implementation, using bridging and anchoring construction 20, the step of translating bridging and anchoring construction 20 in a distal direction relative to delivery catheter's 10, 10' distal end 101, 101' further comprises: using pushtube 202, translating (see e.g., FIG. 9C) bridging and anchoring construction 20 in the distal direction; (see e.g., FIG. 8C) to the point where distal end 2502 (see e.g., FIG. 5A) of jacket 250 abuts target 900, using pushtube 202, distally translating piercing tip 2010 and piercing target 900 with piercing tip 2010. Moreover, the step of engaging target 900 comprises: distally translating piercing tip 2010 into target 900, causing each it lancing members 2010i to transition from a strained configuration inside jacket 250 to unstrained position outside jacket 250, reversing each i$^{th}$ lancing members' 2010i direction toward the interior of target 900 toward the interface of target 900 and article 800 or its portion, thereby engaging target 900 (see e.g., FIG. 6A). In certain implementation, the transition of each i$^{th}$ lancing members' 2010i itself, between the strained configuration inside jacket 250 to unstrained position outside jacket 250 in multiple direction within target 900 is the step causing the engagement between bridging and anchoring construction 20 lancing tip 2010 and target 900. Furthermore, the step of translating bridging and anchoring construction 20 in a proximal direction comprises: using pushtube, 202 translating bridging and anchoring construction 20 in a proximal direction, to the point where target 900 abuts article 800 or its portion (see e.g., FIG. 2C). Yet further, the step of anchoring article 800 or its portion to target 900 comprises: retracting sheath 200 in a proximal direction beyond distal end 2020 of pushtube 202; decoupling pushtube 202 from tubular foreshaft 201; and retracting coupling rod 203 beyond proximal end 2013 of tubular foreshaft 201, and/or retracting (in other words, translating in a proximal direction) sheath 200 beyond proximal end 2013 of tubular foreshaft 201, causing strained proximal region 2012 to transition to its unstrained configuration, hooking article 800 or its portion, thereby anchoring article 800 or its portion to target 900.

Thereafter, the step of translating bridging and anchoring construction 20 in a proximal direction (in other words, pulling the target toward the article) comprises: using pushtube 202, translating bridging and anchoring construction 20 in a proximal direction (pulling), to point where target 900 abuts article 800 or its portion; and the step of anchoring article 800 or its portion to target 900 comprises: retracting sheath 200 in a proximal direction beyond distal end 2020 of pushtube 202; disengaging pushtube 202 from tubular foreshaft 201 (e.g., by disengaging the interlocking T-line interrupted walls 2017 of engaging proximal portion 2014 of tubular foreshaft 201 and T-line interrupted wall 2022 of engaging distal portion 2021 of pushtube 202); and retracting coupling rod 203 beyond proximal end 2013 of tubular foreshaft 201, causing strained proximal region 2012 of tubular foreshaft 201 to transition to unstrained position, forming a hook over article 800 or its portion, thereby anchoring article 800 or its portion to target 900.

In a preliminary step, prior to the step of translating each of bridging and anchoring construction 20, 30, 40, and optionally following the step of transitioning delivery catheter 10 from insertion configuration (see e.g., FIG. 1A) to engagement configuration (see e.g., FIG. 1C), the method further comprises using delivery catheter 10, accommodating at least one bridging and anchoring construction 20, 30, 40, engaging article 800 to abut surface 106, 106' formed by distal end 101 of cylindrical housing 103, and unstrained expander 110.

Additionally, or alternatively, in an exemplary implementation, of using bridging and anchoring construction 30, the step of translating bridging and anchoring construction 30 in a distal direction (in other words, pushing bridging and anchoring construction 30) relative to delivery catheter's 10, 10' distal end 101, 101' comprises: using pushrod 302, translating bridging and anchoring construction 30 in a distal direction (in other words, toward target 900) by pushing distal end 3023 of tab 3021 extending radially from pushrod 302 against distal end 3018 of radial opening 3017, defined in tubular foreshaft's 301 wall, to the point where distal end 2502 of jacket 250 abuts target 900, distally translating piercing tip 3010 into target 900 thereby exposing piercing tip 3010; and piercing target 900 with piercing tip 3010. Consequently, the step of engaging target 900 comprises: further advancing jacket 250 in a distal direction, causing lancing members 3010i, once outside distal end 2502 of jacket 250 to transition to unstrained position outside jacket 250 reversing each i$^{th}$ lancing members' 3010i direction, thereby engaging target 900.

Thereafter, the step of translating bridging and anchoring construction 30 in a proximal direction (pulling target 900 toward article 800 or vice-a-versa) comprises: using pushrod 302, translating bridging and anchoring construction 30 in a proximal direction (toward the target) by pulling tab 3021 extending radially from pushrod 302 against proximal end 3019 of radial opening 3017, defined in tubular foreshaft's 301 wall, to point where target 900 abuts article 800 or its portion, and the step of anchoring article 800 or its portion to target 900 can then comprise: retracting either sheath 200 in a proximal direction beyond proximal end 3013 of tubular foreshaft 301, or retracting coupling rod 303 in a proximal direction beyond proximal end 3013 of tubular foreshaft 301; removing tab 3021 extending radially from pushrod's 302 distal end from radial opening 3017 defined in tubular foreshaft 301; and retracting pushrod 302 in a proximal direction beyond distal end 3013 of tubular foreshaft 301, causing strained proximal region 3012 of tubular foreshaft 301 to transition to unstrained position, hooking article 800 or its portion, thereby anchoring article 800 or its portion to target 900.

Additionally, or alternatively, in yet another exemplary implementation, of using bridging and anchoring construction 40, the step of translating bridging and anchoring construction 40 in distal direction relative to delivery catheter's 10, 10' distal end 101 101' comprises: using pushtube 402, translating bridging and anchoring construction 40 in a distal direction to the point where distal end 2502 of jacket 250 abuts target 900, translating piercing tip 4010 in a distal direction, exposing piercing tip 4010; and piercing target 900 with piercing tip 4010, thereby causing each i$^{th}$ lancing members 4010i to transition to unstrained position outside jacket 250 reversing each i$^{th}$ lancing members' 4010i direction, and thereby engaging target 900. Following engagement of target 900 as described, the step of translating bridging and anchoring construction 40 in a proximal direction comprises: using pushtube 402, translating bridging and anchoring construction 40 in a proximal direction, to a point where target 900 abuts article 800 or its portion. Similarly, albeit different, step of anchoring article 800 or its portion to target 900 comprises: retracting sheath 200 in a proximal direction beyond distal end 4020 of pushtube 402; and rotating pushtube 402 in a direction (clockwise or counter-clockwise) configured to cause pushtube 402 to translate proximally, causing strained proximal portion 4013 of fore-shaft 401 to transition to unstrained position, once proximal end 4014 with pegs 4015, 4015' exit distal end 4020 of pushtube 402, thereby forming a hook over article 800 or its portion, thereby anchoring article 800 or its portion to target 900.

Once article 800 is anchored to the target 900, the method further comprises, decoupling delivery catheter 10 from article 800 or its portion, translating sleeve 100 in a distal direction over the expander 110, transitioning expander 110 from its unstrained position to a strained position; and retracting delivery catheter 10.

Figure 7A:
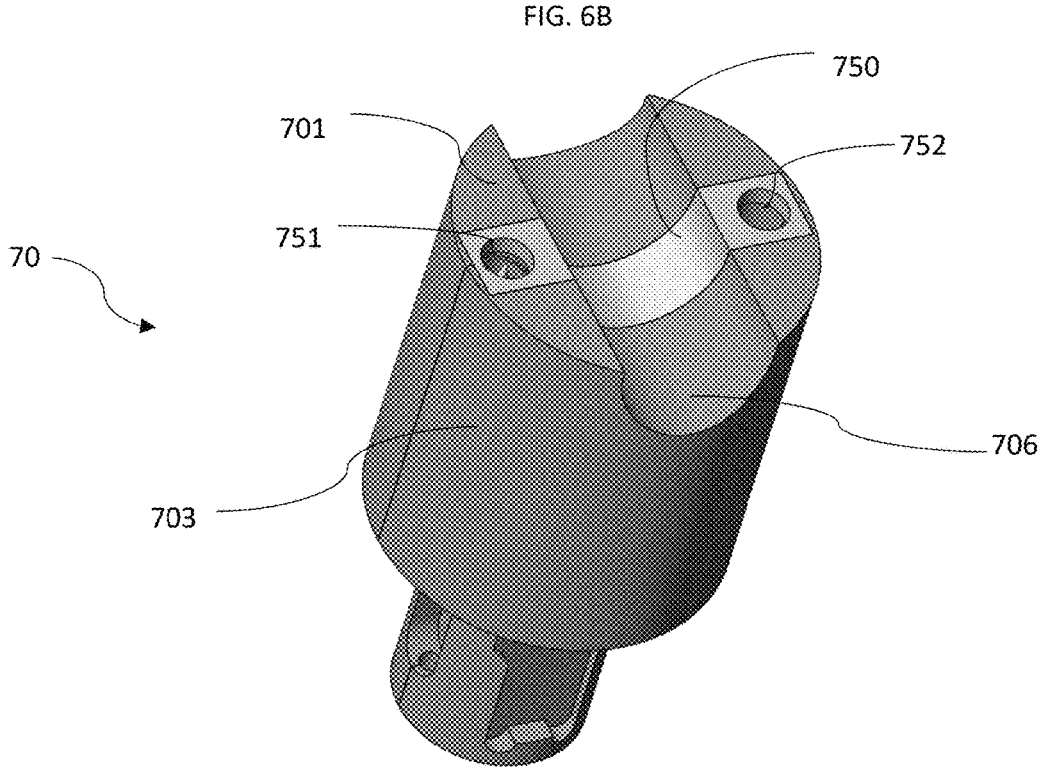
FIG. 7A illustrates another exemplary implementation of the delivery catheter, operable to deliver the bridging and anchoring implementation as illustrated in FIGS. 7B-7E.

FIGS. 7A-8D, illustrate additional exemplary implementations of the system for bridging the gap between an article and a target. For Example, as illustrated in FIG. 7A, delivery catheter head 70, having distal end 701 and arcuate surface 706, accommodating omega-shaped clamp 750, defining pair of apertures 751, 752, sized to accommodate pair of bridging, engaging and anchoring constructs 7000, 7000', each having piercing tip 7010, 7010' and engagement base 703, operable to transition between strained and unstrained configuration within sheath 705. As illustrated, engaging the target on both sides of the article while abutting the delivery catheter 70 against the article to the point the article abuts the target, then distally translating lancing members 7010*i* beyond sheath 705, will initially cause lancing members 7010*i* to expand and further distal translation will transition anchoring base 703 spurs 7030*n*, to unstrain, anchoring clamp 750 over article 800.

Additionally, or alternatively, another exemplary implementation is illustrated in FIGS. 8A-8E, where ratcheting member 85 is operably coupled to cylindrical housing 83 of elongated delivery catheter 80 accommodating bridging, engaging and anchoring constructs 8000, having resilient laddered tail 88, configured upon translation of sheath 81 in a proximal direction, following engagement of the target, and distal translation of elongated delivery catheter 80 toward the target, to cause resilient tail to enter opening 8501 in ratcheting member 85, and engage protruding tab 8502, thereby using ratcheting member 85 as an anchor for the article, once ratcheting member 85 is decoupled from elongated delivery catheter 80.

While in the foregoing specification the methods, systems, sub systems (e.g., bridging and anchoring construction 20, 30, 40) use in bridging the gap between an article or a portion thereof and a target, engaging the target, and anchoring the article or its portion to the target described herein have been described in relation to certain exemplary implementations, and many details are set forth for purpose of illustration, it will be apparent to those skilled in the art that the disclosure of the alignment methods, implementable using the systems disclosed herein are susceptible to additional implementations and that certain of the details described in this specification and as are more fully delineated in the following claims can be varied considerably without departing from the basic principles disclosed herein.

What is claimed is:

1. A system for bridging a gap between an article or a portion thereof and a target, and anchoring the article or its portion to the target, the system comprising:
   a) an elongated delivery catheter having a distal end; and
   b) a bridging and anchoring construction, operable to selectably translate in a distal and a proximal direction relative to the distal end of the elongated delivery catheter, the bridging and anchoring construction slidably coupled to the elongated delivery catheter, wherein the bridging and anchoring construction is operable to:
      i. engage the target following the distal translation spanning the gap between the article or its portion and the target;
      ii. eliminate the gap following the proximal translation of the bridging and anchoring construction thereby pulling the article or a portion thereof towards the target; and
      iii. anchor the article or its portion to the target,
   wherein the target is a structural heart valve.

2. The system of claim 1, wherein the delivery catheter is operable to transition between an insertion configuration and engagement configuration, wherein the distal end is contoured to abut at least a portion of the article or its portion's surface in its engagement configuration, the elongated delivery catheter further comprises:
   a) a cylindrical sleeve, operable to slidably translate in a proximal direction; and
   b) a cylindrical housing, defining a through bore, sized to accommodate the bridging and anchoring construction, the cylindrical housing having a distal end with an arcuate cross section sized to abut between about 1.0 radians, and about 4.5 radians of the at least portion of the article or its portion's surface.

3. The system of claim 2, wherein the cylindrical housing further comprises an expander, operable to transition between a strained position within the sleeve and an unstrained position outside the sleeve, wherein, in the unstrained position, a distal portion of the expander forms a complimentary arcuate cross section to the arcuate cross section of the distal end of the housing.

4. The system of claim 2, wherein the bridging and anchoring construction comprises:
   a) a jacket;
   b) at least one of: a coupling rod, sized to be accommodated coaxially within a pushtube, and a sheath nested within the jacket;
   c) a piercing tip comprised of a plurality of lancing members configured to transition between a strained position within the jacket and an unstrained position outside the jacket;
   d) a tubular foreshaft having a proximal end, the tubular foreshaft coupled proximally to the piercing tip, comprising:
      i. a proximal region configured to transition between a strained position when coupled to at least one of: a coupling rod, and a sheath, and an unstrained position following proximally translating at least one of: the coupling rod inserted coaxially within the tubular foreshaft wherein and the sheath;
      ii. a proximal end forming a portion of the proximal region, the proximal end operable to form an engagement section with a T-line interrupted wall; and e) the pushtube, having a distal end operable to form an engagement section with a T-line interrupted wall, complementary to the engagement section of the tubular foreshaft, releasably coupled coaxially to the proximal end of the tubular foreshaft.

5. The system of claim 4, wherein the coupling rod extends into the tubular foreshaft in a distal direction beyond the strained proximal region.

6. The system of claim 2, wherein the bridging and anchoring construction comprises:

a) a jacket, b) at least one of: a coupling rod, sized to be accommodated coaxially within a tubular foreshaft, and a sheath, nested within the jacket;

c) a piercing tip comprised of a plurality of lancing members configured to transition between a strained position within the jacket and an unstrained position outside the jacket;

d) the tubular foreshaft having a proximal end, the tubular foreshaft coupled proximally to the piercing tip, comprising: i. a proximal region configured to transition between a strained position when coupled to a pushrod inserted coaxially within the tubular foreshaft and at least one of: a coupling rod, and a sheath, and an unstrained position following decoupling the pushrod and the at least one of: the coupling rod, and the sheath; and ii. a radial opening, defined in the tubular foreshaft's wall, the radial opening defined distal to the proximal region, having a proximal end and a distal end, the radial opening sized to accommodate a distal portion of the pushrod, e) the pushrod, with the distal portion extending radially from the pushrod's distal end, wherein the distal portion forms a tab extending radially from the pushrod to a distance W is larger than the radius of an internal diameter of the tubular foreshaft and smaller than the internal diameter of the tubular foreshaft and wherein the proximal portion of the pushrod has an outer diameter that is not larger than the radius of the internal diameter of the cylindrical foreshaft.

7. The system of claim 6, wherein the coupling rod, extends in a distal direction beyond the strained proximal region, wherein the coupling rod has an outer diameter that is not larger than the radius of the internal diameter of the cylindrical foreshaft.

8. The system of claim 2, wherein the bridging and anchoring construction comprises:

a) a jacket;

b) a sheath;

c) a piercing tip comprised of a plurality of lancing members configured to transition between a strained position within the jacket and an unstrained position outside the jacket;

d) a pushtube, having a distal portion defining a helical wall channel, the helical wall channel having a predetermined pitch, configured to engage a proximal portion of a foreshaft; and e) the foreshaft having a distal end coupled to the piercing tip, and a proximal portion with a proximal end with a pair of diametrically opposed pegs extending radially from the proximal end of the foreshaft wherein:

i. the pair of diametrically opposed pegs extending laterally being sized and configured to be accommodated in the helical wall channel of the pushtube; and ii. the proximal portion is configured to transition between a strained position while coupled to at least one of: the pushtube and the sheath, and an unstrained position when decoupled from the at least one of: the pushtube and the sheath.

9. A method for bridging a gap between an article or a portion thereof and a target, and anchoring the article or its portion to the target, the method implementable in a system comprising an elongated delivery catheter having a distal end; and a bridging and anchoring construction, operable to selectably translate in a distal and a proximal direction relative to the distal end of the elongated delivery catheter, the bridging and anchoring construction slidably coupled to the elongated delivery catheter, wherein the bridging and anchoring construction is operable to engage the target following a distal translation spanning the gap between the article or its portion and the target; eliminating the gap following a proximal translation of the bridging an anchoring construction thereby pulling the article or a portion thereof towards the target; and anchoring the article or its portion to the target, the method comprising:

a) inserting the delivery catheter;

b) partially engaging the article or its portion to the delivery catheter;

c) translating the bridging and anchoring construction in a distal direction relative to the delivery catheter's distal end over the gap;

d) using the bridging and anchoring construction engaging the target;

e) translating the bridging and anchoring construction in a proximal direction relative to the delivery catheter's distal end thereby pulling the article or a portion thereof towards the target to the point where the target abuts the article or its portion; and f) using the bridging and anchoring construction anchoring the article or its portion to the target, wherein the target is a structural heart valve.

10. The method of claim 9, wherein the delivery catheter is operable to transition between an insertion configuration and engagement configuration, wherein the distal end is contoured to abut at least a portion of the article or its portion's surface in its engagement configuration, the elongated delivery catheter further comprises:

a) a cylindrical sleeve, operable to slidably translate in at least one of: a proximal direction, and a distal direction;

b) a cylindrical housing, defining a through bore, sized to accommodate the bridging and anchoring construction, the cylindrical housing having a distal end with an arcuate cross section sized to abut between about 1.0 radians, and about 4.5 radians of the at least portion of the article or its portion's surface; and c) an expander, operable to transition between a strained position within the sleeve and an unstrained position outside the sleeve, wherein, in the unstrained position, a distal portion of the expander forms a complimentary arcuate cross section to the arcuate cross section of the distal end of the housing.

11. The method of claim 10, wherein the step of transitioning the delivery catheter from the insertion configuration to the engagement configuration comprises retracting the sleeve in a proximal direction, causing the expander to transition to the unstrained position.

12. The method of claim 11, further comprises: using a surface created by the distal end of the delivery catheter cylindrical housing and the unstrained expander, coupling the delivery catheter to the article or a portion thereof.

13. The method of claim 12, further comprising:

a) Decoupling the delivery catheter from the article or its portion;

b) translating the sleeve in a distal direction over the expander, transitioning the expander from the unstrained position to the strained position; and c) retracting the delivery catheter.

14. The method of claim 9, wherein the gap between the article or its portion and the target, is between about 0.01 mm and about 40 mm.

15. The method of claim 14, wherein, using the bridging and anchoring construction of claim 4, the step of translating the bridging and anchoring construction in a distal direction relative to the delivery catheter's distal end further comprises:

a) using the pushtube, translating the bridging and anchoring construction in the distal direction to the point where the distal end of the jacket abuts the target; and b) translating the piercing tip in a distal direction, thereby piercing the target with the piercing tip.

16. The method of claim 15, wherein the step of engaging the target comprises: following piercing the target, further translating the piercing tip in a distal direction, causing the lancing members to transition to the unstrained position outside the jacket's distal end, reversing the lancing members' direction, thereby engaging the target.

17. The method of claim 16, wherein the step of translating the bridging and anchoring construction in a proximal direction comprises: using the pushtube, translating the bridging and anchoring construction in a proximal direction, to the point where the target abuts the article or its portion.

18. The method of claim 17, wherein the step of anchoring the article or its portion to the target comprises at least one of:

a) retracting at least one of: the coupling rod, and the sheath in a proximal direction beyond the distal end of the pushtube, b) decoupling the pushtube from the tubular foreshaft, and c) retracting at least one of: the coupling rod, and the shaft beyond the proximal end of the tubular foreshaft, causing the strained proximal region to transition to the unstrained position, hooking the article or its portion, thereby anchoring the article or its portion to the target.

19. The method of claim 14, wherein, using the bridging and anchoring construction of claim 6, the step of translating the bridging and anchoring construction in a distal direction relative to the delivery catheter's distal end further comprises:

a) using the pushrod, translating the bridging and anchoring construction in a distal direction by pushing the tab extending radially from the pushrod against the distal end of the radial opening, defined in the tubular foreshaft's wall to the point where the distal end of the jacket abuts the target; and;

b) translating the piercing tip in a distal direction, exposing the piercing tip and penetrating the target with the piercing tip.

20. The method of claim 19, wherein the step of engaging the target comprises: further translating the piercing tip in a distal direction, causing the lancing members, once beyond the distal end of the jacket to transition to the unstrained position outside the jacket, reversing the lancing members' direction, thereby engaging the target.

21. The method of claim 20, wherein the step of translating the bridging and anchoring construction in a proximal direction comprises: using the pushrod, translating the bridging and anchoring construction in a proximal direction by pulling the tab extending radially from the pushrod against the proximal end of the radial opening, defined in the tubular foreshaft's wall, to the point where the target abuts the article or its portion.

22. The method of claim 21, wherein the step of anchoring the article or its portion to the target comprises:

a) retracting at least one of: the coupling rod in a proximal direction beyond the proximal end of the tubular foreshaft, and the sheath in a proximal direction beyond the proximal end of the tubular foreshaft;

b) removing the tab extending radially from the pushrod's distal end from the radial opening defined in the tubular foreshaft; and c) retracting the pushrod in a proximal direction beyond the distal end of the tubular foreshaft, causing the strained proximal region of the tubular foreshaft to transition to the unstrained position, hooking the article or its portion, thereby anchoring the article or its portion to the target.

23. The method of claim 22, wherein the step of engaging the target comprises: further retracting the piercing tip in a distal direction and penetrating the target, causing the lancing members to transition to the unstrained position once beyond the distal end of the jacket, thereby reversing the lancing members' direction and engaging the target.

24. The method of claim 23, wherein the step of translating the bridging and anchoring construction in a proximal direction comprises: using the pushtube, translating the bridging and anchoring construction in a proximal direction, to the point where the target abuts the article or its portion.

25. The method of claim 24, wherein the step of anchoring the article or its portion to the target comprises:

a) retracting the sheath in a proximal direction beyond the distal end of the pushtube; and b) rotating the pushtube in a direction configured to cause the pushtube to translate proximally, causing the strained proximal region of the foreshaft to transition to the unstrained position, hooking the article or its portion, thereby anchoring the article or its portion to the target.

26. The method of claim 14, wherein, using the bridging and anchoring construction of claim 8, the step of translating the bridging and anchoring construction in a distal direction relative to the delivery catheter's distal end further comprises:

a) using the pushtube, translating the bridging and anchoring construction in a distal direction to the point where the distal end of the jacket abuts the target;

b) translating the jacket in a proximal direction, exposing the piercing tip; and c) piercing the target with the piercing tip.

27. The method of claim 9, wherein the structural heart valve comprises an annulus, and wherein the anchoring comprises anchoring the article or its portion to the annulus of the structural heart valve.

28. The method of claim 9, wherein the structural heart valve is a mitral valve, a tricuspid valve, or a pulmonary valve.

29. The method of claim 28, wherein the article is an annuloplasty ring or a portion thereof.

30. The method of claim 29 wherein anchoring the annuloplasty ring or its portion is configured to anchor the annuloplasty ring or its portion to a trigon.

31. A use of a gap bridging and anchoring system in the process of bridging a gap between an article or a portion thereof and a target, and in the process of anchoring the article or its portion to the target, the system comprising:

c) an elongated delivery catheter having a distal end; and d) a bridging and anchoring construction, operable to selectably translate in a distal and a proximal direction relative to the distal end of the elongated delivery catheter, the bridging and anchoring construction slidably coupled to the elongated delivery catheter, wherein the bridging and anchoring construction is operable to:

i. engage the target following a distal translation spanning the gap between the article or its portion and the target;

ii. eliminate the gap following a proximal translation of the bridging and anchoring construction thereby pulling the article or a portion thereof towards the target; and iii. anchor the article or its portion to the target, wherein the target is a structural heart valve.

32. The use of claim 31, wherein the delivery catheter is operable to transition between an insertion configuration and engagement configuration, wherein the distal end is contoured to abut at least a portion of the article or its portion's surface in its engagement configuration, the elongated delivery catheter further comprises:

a) a cylindrical sleeve, operable to slidably translate in a proximal direction;

b) a cylindrical housing, defining a through bore, sized to accommodate the bridging and anchoring construction, the cylindrical housing having a distal end with an arcuate cross section sized to abut between about 1.0 radians, and about 4.5 radians of the at least portion of the article or its portion's surface; and c) an expander, operable to transition between a strained position within the sleeve and an unstrained position outside the sleeve, wherein, in the unstrained position, a distal portion of the expander forms a complimentary arcuate cross section to the arcuate cross section of the distal end of the housing.

33. The use of claim 31, wherein the bridging and anchoring construction comprises:

a) a jacket;

b) at least one of: a coupling rod, sized to be accommodated coaxially within a pushtube, and a sheath nested within the jacket;

c) a piercing tip comprised of a plurality of lancing members configured to transition between a strained position within the jacket and an unstrained position outside the jacket;

d) a tubular foreshaft having a proximal end, the tubular foreshaft coupled proximally to the piercing tip, comprising: i. a proximal region configured to transition between a strained position when coupled to at least one of: a coupling rod, and a sheath, and an unstrained position following proximally translating at least one of: the coupling rod inserted coaxially within the tubular foreshaft wherein and the sheath; ii. a proximal end forming a portion of the proximal region, the proximal end operable to form an engagement section with a T-line interrupted wall; and e) the pushtube, having a distal end operable to form an engagement section with a T-line interrupted wall, complementary to the engagement section of the tubular foreshaft, releasably coupled coaxially to the proximal end of the tubular foreshaft.

34. The use of claim 31, wherein the bridging and anchoring construction comprises:

a) a jacket, b) at least one of: a coupling rod, sized to be accommodated coaxially within a tubular foreshaft, and a sheath, nested within the jacket;

c) a piercing tip comprised of a plurality of lancing members configured to transition between a strained position within the jacket and an unstrained position outside the jacket;

d) the tubular foreshaft having a proximal end, the tubular foreshaft coupled proximally to the piercing tip, comprising:

i. a proximal region configured to transition between a strained position when coupled to a pushrod inserted coaxially within the tubular foreshaft and at least one of: a coupling rod, and a sheath, and an unstrained position following decoupling the pushrod and the at least one of: the coupling rod, and the sheath; and ii. a radial opening, defined in the tubular foreshaft's wall, the radial opening defined distal to the proximal region, having a proximal end and a distal end, the radial opening sized to accommodate a distal portion of the pushrod, e) a pushrod, with the distal portion extending radially from the pushrod's distal end, wherein the distal portion forms a tab extending radially from the pushrod to a distance W is larger than the radius of an internal diameter of the tubular foreshaft and smaller than the internal diameter of the tubular foreshaft and wherein the proximal portion of the pushrod has an outer diameter that is not larger than the radius of the internal diameter of the cylindrical foreshaft.

35. The use of claim 31, wherein the bridging and anchoring construction comprises:

a) a jacket;

b) a sheath;

c) a piercing tip comprised of a plurality of lancing members configured to transition between a strained position within the jacket and an unstrained position outside the jacket;

d) a pushtube, having a distal portion defining a helical wall channel, the helical wall channel having a predetermined pitch, configured to engage a proximal portion of a foreshaft; and e) the foreshaft having a distal end coupled to the piercing tip, and a proximal portion with a proximal end with a pair of diametrically opposed pegs extending radially from the proximal end of the foreshaft wherein:

i. the pair of diametrically opposed pegs extending laterally being sized and configured to be accommodated in the helical wall channel of the pushtube; and ii. the proximal portion is configured to transition between a strained position while coupled to at least one of: the pushtube and the sheath, and an unstrained position when decoupled from the at least one of: the pushtube and the sheath.

36. The use of claim 31, wherein the structural heart valve comprises an annulus, and wherein the anchoring comprises anchoring the article or its portion to the annulus of the structural heart valve.

37. The use of claim 31, wherein the structural heart valve is a mitral valve, a tricuspid valve, or a pulmonary valve.

38. The use of claim 37, wherein the article is an annuloplasty ring or a portion thereof.

39. The use of claim 38 wherein anchoring the annuloplasty ring or its portion is configured to anchor the annuloplasty ring or its portion to a trigon.

\* \* \* \* \*